United States Patent
Davis et al.

(10) Patent No.: US 9,212,395 B2
(45) Date of Patent: Dec. 15, 2015

(54) HAPLOTYPE TAGGING SINGLE NUCLEOTIDE POLYMORPHISMS AND USE OF SAME TO PREDICT CHILDHOOD LYMPHOBLASTIC LEUKEMIA

(75) Inventors: Charronne Florence Davis, Elkins Park, PA (US); Mehmet Tevfik Dorak, Pembroke, FL (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 0 days.

(21) Appl. No.: 12/658,269

(22) Filed: Feb. 9, 2010

(65) Prior Publication Data

US 2011/0086346 A1  Apr. 14, 2011

Related U.S. Application Data

(60) Provisional application No. 61/208,377, filed on Feb. 23, 2009.

(51) Int. Cl.
*C12Q 1/68* (2006.01)
*C07H 21/02* (2006.01)
*C07H 21/04* (2006.01)

(52) U.S. Cl.
CPC ........ *C12Q 1/6886* (2013.01); *C12Q 2600/156* (2013.01); *Y10T 436/143333* (2015.01)

(58) Field of Classification Search
None
See application file for complete search history.

(56) References Cited

U.S. PATENT DOCUMENTS

2002/0182622 A1* 12/2002 Nakamura et al. ............... 435/6
2010/0092959 A1* 4/2010 Dorak et al. ............... 435/6

OTHER PUBLICATIONS

Davis et al. American Society for Histocompatibility and Immunogenetics. 2008. Meeting held Oct. 30, 2008. Pub No. 36-OR.*
NCBI Database. National Center for Biotechnology Information. National Library of Medicine, NIH (Bethesda, MD, USA) rs807212, ss65842256, Oct. 17, 2006.*
NCBI Database. National Center for Biotechnology Information. National Library of Medicine, NIH (Bethesda, MD, USA) rs807212, available at url: <http://www.ncbi.nlm.nih.gov/projects/SNP/snp_ref.cgi?rs=807212 >, printed on Mar. 19, 2012.*
Hirschhorn et al. Genetics in Medicine. vol. 4, No. 2, pp. 45-61, Mar. 2002.*
Lucentini et al. The Scientist (2004) vol. 18, p. 20.*
Halushka et al. Nature. Jul. 1999. 22: 239-247.*
Ioannidis et al. Nature genetics (2001) 29:306-309.*
Albig, Werner et al., Journal of Cellular Biochemistry 69:117-126 (1998).
Campbell, Harry et al., Human Molecular Genetics, 2007, vol. 16, No. 2, 233-241.
Dorak, M. T. et al., Blood, 1999, 94(11):3957.
Dorak, M. T. et al., Genet. Med. 2005: 7(3): 159-168.
Dorak, M. T. et al., Leukemia Research 26 (2002) 651-656.
Dorak, M. T. et al., Cancer Causes Control (2007) 18: 219-228.
Gubbels Bupp, M. R. et al., Genes and Immunity (2008) 9, 47-56.
Porto, Graca et al., World J. Gastroenterol. Sep. 21, 2007; 13(35): 4707-4715.
Fisher, J. et al., Am. J. Physiol. Cell Physiol. 293: 641-649, 2007.
Hannuksela, Jokke et al., Haematologica 2002; 87: 131-135.

* cited by examiner

*Primary Examiner* — Carla Myers
(74) *Attorney, Agent, or Firm* — Siu K. Lo

(57) ABSTRACT

The present invention is directed to novel haplotype tagging single nucleotide polymorphisms (SNPs) in specific regions outside the HFE gene that serve as a reliable biomarker for a decreased risk for childhood lymphoblastic leukemia (ALL) in a child. There is provided herein methods and reagents for assessing the haplotype tagging SNPs selected from the group consisting of rs807212, rs198853, rs9467664, rs2213284, rs2230655 and rs12346. The method useful in applying these SNPs in predicting a decreased risk of childhood lymphoblastic leukemia (ALL) is also disclosed.

4 Claims, 4 Drawing Sheets

Figure 1. LD plot showing correlation coefficient ($r^2 \times 100$) values as LD parameter in controls. Haplotype blocks were obtained by using the default confidence intervals option of Haploview.

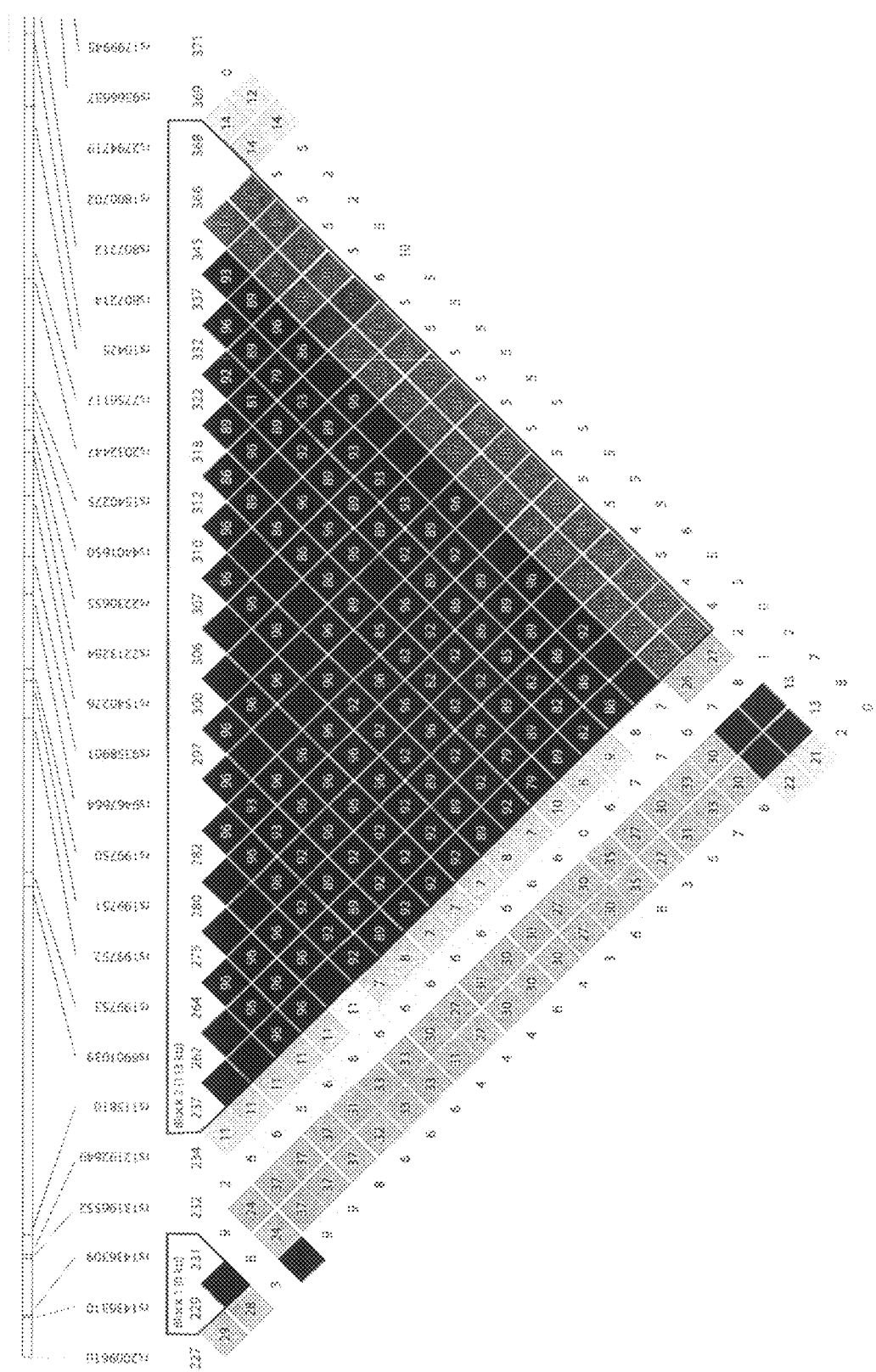

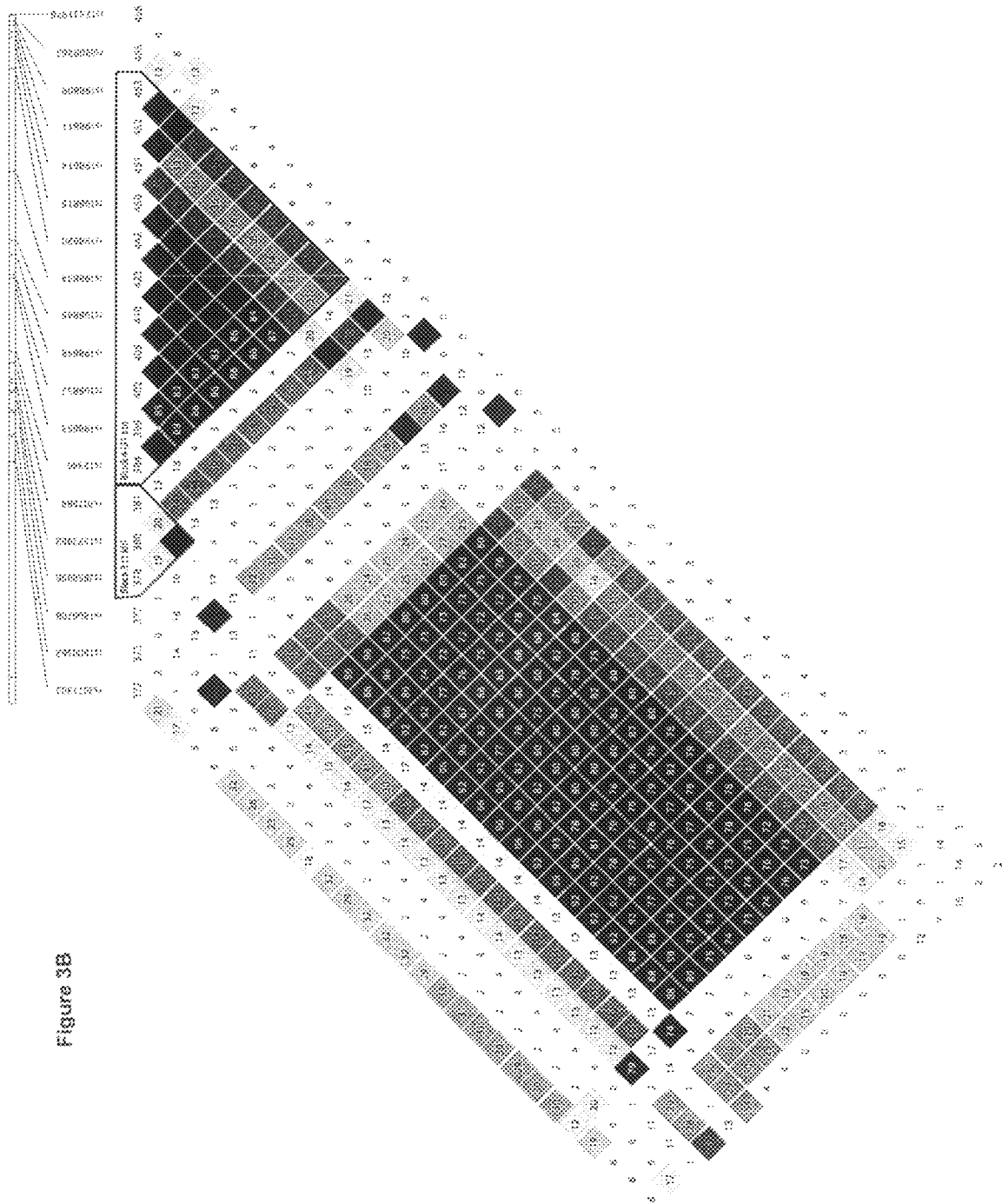

HAPLOTYPE TAGGING SINGLE NUCLEOTIDE POLYMORPHISMS AND USE OF SAME TO PREDICT CHILDHOOD LYMPHOBLASTIC LEUKEMIA

CROSS-REFERENCE TO RELATED APPLICATIONS

The present application claims the benefit under 35 U.S.C. §119(e) to U.S. Provisional Applications No. 61/208,377 filed Feb. 23, 2009, the content of which is incorporated by reference herein in their entirety.

BACKGROUND OF THE INVENTION

HFE (High Iron Fe) gene encodes the human hemochromatosis protein (HFE protein) which regulates iron homeostasis and can cause the iron overload disorder hereditary hemochromatosis. The HFE gene is located on short arm of chromosome 6 at location 6p21.3. Because iron is required during cell proliferation, excess of iron has been implicated in cancer development (Stevens et al., 1994; Dorak et al., 2005). C282Y (rs1800562) is a single nucleotide polymorphism (SNP) present in the HFE gene and represents the most common genetic mutation of the HFE gene.

Single nucleotide polymorphism (SNP) may influence gene functions and modifies an individual's susceptibility to diseases, such as cancers. In some instances, a single SNP may be sufficient to confer susceptibility, while in others multiple SNPs may act jointly to influence disease susceptibility. There are at least five (5) SNPs that are present within the HFE gene. C282Y (rs180052) in the HFE gene was first reported to be a risk marker for childhood acute lymphoblastic leukemia (ALL) in Welsh population (Dorak et al. 1999). Since then, there has been no report suggesting the presence of other SNPs within the HFE gene that may directly be associated with childhood ALL. Within the HFE gene, H63D (rs1799945) has been shown to associate with iron overload in the European population (Porto et al., 1998), whereas rs9366637 association is shown in the Asian population (Dorak et al., 2009). It has been speculated that SNPs such as H63D and rs9366637 present in the HFE gene may modify the risk of cancers (Dorak et al., 2006) by virtue of their ability to regulate iron homeostasis. However, a direct association between H63D and rs9366637 and childhood ALL has not been established, other than their potential association with iron overload.

The original observation that C282Y is associated with childhood ALL in Wales and Scotland has not been reproduced and confirmed by others when this particular SNP was evaluated in Mexican and Finnish populations (Ruiz-Argüelles et al., 2006; Hannuksela et al., 2007). This raises the issue of general applicability to use C282Y as a genetic marker for childhood ALL. Failure to replicate a genetic association from one population group to another is common. In the case of C282Y, the underlying basis for the discrepancy is presently unclear. Possible explanations may include differences in population-specific linkage disequilibrium (LD) patterns in the HFE region, or differences in genetic and environmental modifiers among populations.

To the best of the present inventors' knowledge, there are no reliable SNP as a genetic marker to predict the childhood ALL. Yet, there is a continuing need for a genetic marker to predict the probability of childhood ALL. The need for a reliable tagging SNP biomarker for childhood ALL is expected to have utility in the application in child leukemia clinics.

BRIEF SUMMARY OF THE INVENTION

The present invention is based on the finding that a haplotype tagging SNP in the vicinity of the HFE gene represents a reliable biomarker candidate in predicting a reduced risk of childhood acute lymphoblastic leukemia (ALL) in a child.

In accordance with the present invention, the presence of a haplotype tagging SNP selected from the group consisting of rs807212, rs198853, rs9467664, rs2213284, rs2230655 and rs12346 influence childhood ALL. The presence of a haplotype tagging SNP correlates with the absence of all three (3) pathogenic SNPs (that are associated with childhood ALL). Because of the absence of these 3 pathogenic SNPs, the presence of a haplotype tagging SNP indicates a reduced risk of childhood ALL. There is disclosed herein a method of assessing the haplotype SNPs in a biological sample derived from a human, such as a child.

In one aspect, the present invention provides a panel of haplotype tagging SNPs that predict the reduced risk for childhood ALL and methods of using these SNPs in assessing the risk of developing childhood ALL.

In one aspect, the present inventors provides direct evidence for two (2) haplotype tagging SNPs (i.e., rs807212 and rs198853) within the 152 kb region, the presence of which indicates the absence of the three (3) pathogenic SNPs. The presence of either rs807212 or rs198853 serve as an indicator for a reduced risk in childhood ALL.

In one aspect, the present inventors further provide evidence that there are four (4) SNPs within the 152 kb region, that are closely linked (i.e., having a correlation coefficient ($r^2$)≥0.9) to the haplotype tagging SNP rs807212. Accordingly, these four (4) SNPs (namely, rs9467664, rs2213284, rs2230655 and rs12346) are functionally equivalent as to that of the two (2) haplotype tagging SNPs (i.e., rs807212 and rs198853), and serve as an indicator for a reduced risk in childhood ALL.

In one aspect, the present invention provides a panel of haplotype tagging SNPs selected from the group consisting of rs807212 and rs198853 as a predictor for a risked risk in childhood ALL.

In another aspect, the present invention further provides a panel of haplotype tagging SNPs selected from the group consisting of rs9467664, rs2213284, rs2230655 and rs12346 that can similarly serve as a predictor for a reduced risk of childhood ALL.

In another aspect, the present invention provides a method for predicting childhood acute lymphoblastic leukemia (ALL) in a child, comprising the steps of: (a) providing a biological sample; (b) isolating nucleic acid from said sample; and (c) assessing the presence of a haplotype tagging SNP selected from the group consisting of rs807212, rs198853, rs9467664, rs2213284, rs2230655 and rs12346, wherein the presence of said haplotype tagging SNP is indicative of a reduced risk of childhood acute lymphoblastic leukemia in said child.

Preferably, the haplotype tagging SNP is rs807212. Preferably, the haplotype tagging SNP is rs198853.

Preferably, the biological sample is derived from core blood from an infant or peripheral blood from a child.

In another aspect, the present invention provides an isolating step to be performed using phenol-chloroform. Preferably, the nucleic acid is genomic DNA.

In one aspect, the present invention provides a method of detecting a haplotype tagging SNP using an assessing step performed by TaqMan allelic discrimination assay, high resolution melting assay, or polymerase chain reaction-restriction fragment length polymorphism assay. Preferably, the assessing step is performed by TaqMan allelic discrimination assay.

In another aspect, the present invention provides a method of predicting childhood acute lymphoblastic leukemia (ALL) in a child, comprising the steps of: (a) providing a biological sample; (b) isolating nucleic acid from said sample; and (c) assessing the presence of a haplotype tagging SNP rs807212 by performing a TaqMan allelic discrimination assay, wherein the presence of said haplotype tagging SNP is indicative of a protective marker for childhood acute lymphoblastic leukemia (ALL) in said child.

BRIEF DESCRIPTION OF THE DRAWINGS

FIGS. 3A and 3B depict a 152 kb block that includes 26 single nucleotide polymorphisms (SNPs) tightly in linkage disequilibrium with each other flanking the HFE gene.

DETAILED DESCRIPTION OF THE INVENTION

Figure 1:
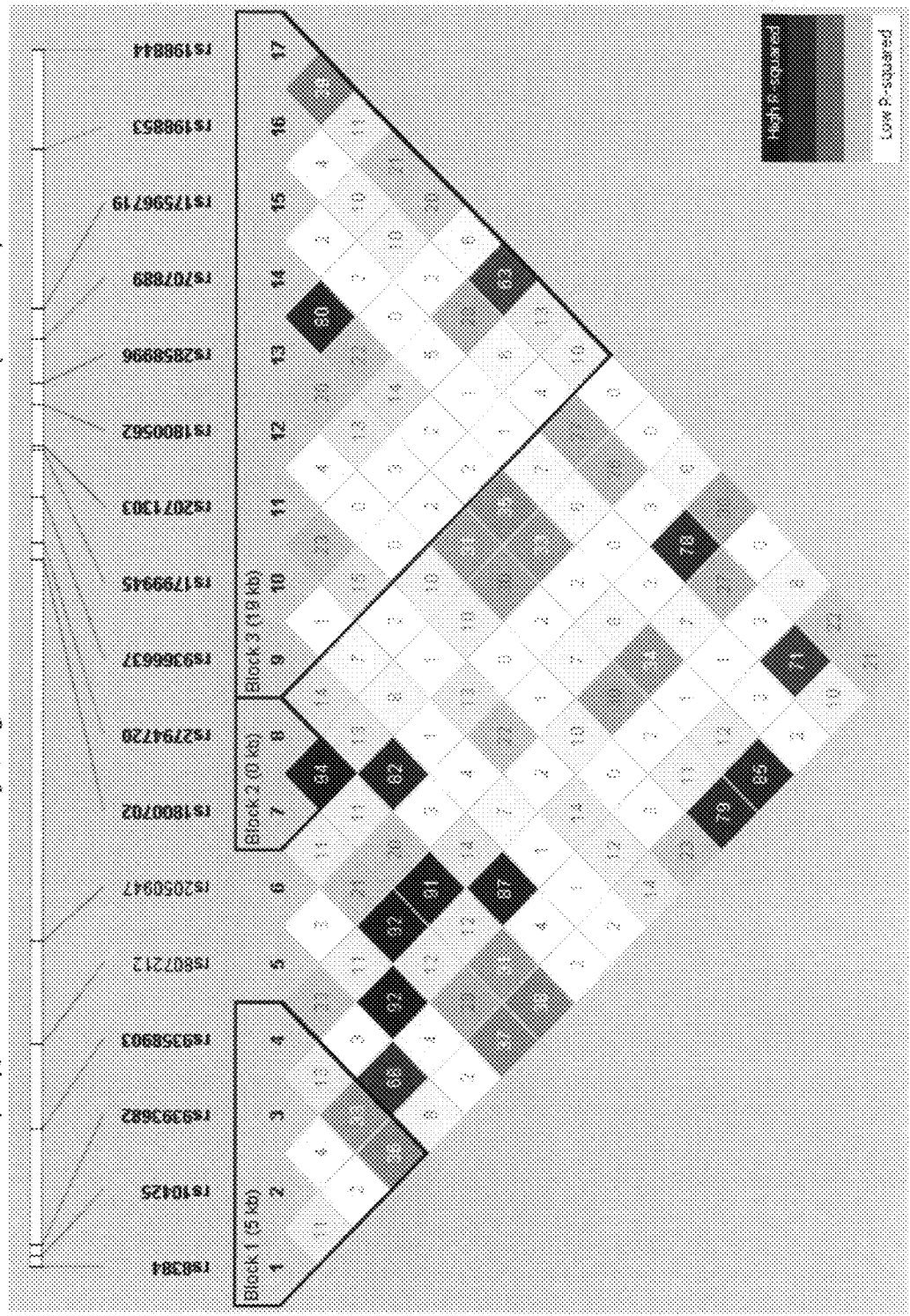
FIG. 1 depicts a Linkage Disequilibrium (LD) plot showing the correlation coefficient ($r^2 \times 100$) values as a measure of LD relationship in the Welsh controls. The areas within the thick spine (i.e., the bold line) represent the haplotype blocks. There are three (3) haplotype blocks in this figure; namely block 1, block 2 and block 3). The thick spine was calculated by using the default confidence intervals option of Haploview. High R-squared represents a high LD between the two variants on the diagonals. Low R-squared indicates a low LD between the two variants. The intensity of the color represents the value of the correlation coefficient. The darker the color, the higher the correlation coefficient (i.e., higher $r^2$ value). Note that the haplotype tagging SNP rs807212 is not in the same haplotype block as the SNPs located in the HFE gene (i.e., HFE gene spans from rs1800702 to rs707889). rs807212, however, has a strong correlation coefficient with rs198853 (which is outside the HFE gene).

The present inventors cured the prior art deficiency and have identified a haplotype tagging single nucleotide polymorphism (SNP) that reliably predicts the risk of acute lymphoblastic leukemia (ALL) in a child. The presence of such haplotype tagging SNPs indicates the absence of three (3) pathogenic SNPs (i.e., rs9366637, rs1799945 and rs1800562). Therefore, the present invention provides an accurate and reliable genetic marker (i.e., haplotype tagging SNPs) in a child in predicting childhood ALL. The present inventors discovered that specific haplotype single nucleotide polymorphisms (SNPs) outside of the HFE gene represent good predictors for protecting a child from inflicting childhood ALL.

Definitions:

Various terms used throughout this specification shall have the definitions set forth herein.

The term "HFE" refers to the hemochromatosis gene. The HFE gene encodes a membrane protein that is similar to MHC class I-type proteins and interacts with $beta_2$-microglobulin ($beta_2M$). The nucleotide sequence of the HFE gene has been deposited in the NCBI with an accession number (i.e., GeneID is 3077).

The term "polymorphism" refers to the occurrence of two or more alternative genomic sequences or alleles between or among different genomes or individuals.

The term "locus" is the site along a chromosome where a polymorphism occurs. A polymorphic locus may be as small as one base pair, in which case it is referred to as single nucleotide polymorphism (SNP). The first identified allelic form is arbitrarily designated as the reference, wild-type, common or major form, and other allelic forms are designated as alternative, minor, rare or variant alleles.

The term "genotype" refers to a description of the alleles of a gene contained in an individual or sample.

The term "single nucleotide polymorphism" ("SNP") refers to a site of one nucleotide that varies between alleles.

The term "functional SNPs" refers to those SNPs that produce alterations in gene expression or in the expression or function of a gene product, and therefore are most predictive of a possible clinical phenotype. The alterations in gene function caused by functional SNPs may include changes in the encoded polypeptide, changes in mRNA stability, binding of transcriptional and translation factors to the DNA or RNA, and the like.

The term "pathogenic SNP" refers to a functional SNP that causes a disease. For purposes of this application, three (3) pathogenic SNPs are included; namely rs1800562, rs9366637 and rs1799945. The rs1800562 has been attributed to cause iron overload and childhood ALL. rs9366637 and rs1799945 are known to cause iron overload, which may indirect affect the development of childhood ALL.

The term "variant allele" refers to the allele that is different from the consensus sequence at a particular locus.

The term "haplotype tagging SNPs" (htSNPs) refers to a subset of SNPs in each gene that provides sufficient information about genetic variation in a gene as genotyping all of the SNPs in a gene. They basically represent other SNPs in their vicinity and make the others redundant in terms of providing additional information about genetic variation.

The term "oligonucleotide" is used interchangeable with "primer" or "polynucleotide."

The term "primer" refers to an oligonucleotide that acts as a point of initiation of DNA synthesis in a PCR reaction. A primer is usually about 15 to about 35 nucleotides in length and hybridizes to a region complementary to the target sequence.

The term "probe" refers to an oligonucleotide that hybridizes to a target nucleic acid in a PCR reaction. Target sequence refers to a region of nucleic acid that is to be analyzed and comprises the polymorphic site of interest.

The term "TaqMan allelic discrimination assay" (also known as the 5' nuclease PCR assay) is a technology that exploits the 5'-3' nuclease activity of Taq DNA polymerase to allow direct detection of the PCR product by the release of a fluorescent report as a result of PCR. The TaqMan allelic discrimination assay permits discrimination between the alleles of a two-allele system. It represents a sensitive and rapid means of genotyping SNPs.

The term "PCR-RFLP" refers to polymerase chain reaction-restriction fragment length polymorphism. PCR-RFLP is technique to detect a variation in the DNA sequence of a genome by breaking the DNA into pieces with restriction enzymes and analyzing the size of the resulting fragments by gel electrophoresis. PCR-RFLP is one type of genotyping for detecting SNP by visualization of fragments on a gel following restriction endonuclease digestion of the PCR product.

The term "HRM" refers to high resolution melting. FIRM is a technique to detect a genetic variation by binding a probe to a DNA fragment, then gradually denaturing the two fluorescent strands. The denaturation results in the loss of fluorescence and the alleles can be differentiated by the rate of fluorescence lost over temperature.

The term "95% confidence interval" (or "95% CI") refers to the range of values surrounding the odds ratio (OR) within which the true value is believed to lie with 95% certainty.

The term "Hardy-Weinberg equilibrium" refers to a principle that allele and genotype frequencies in a population remain constant; that is, they are in equilibrium-from generation to generation unless specific disturbing influences are introduced. Those disturbing influences include non-random mating, mutations, selection, limited population size, random genetic drift and gene flow. In the simplest case of a single locus with two alleles: one allele is denoted "A" and the other "a" and their frequencies are denoted by p and q; freq(A)=p; freq(a)=q; p+q=1. According to the Hardy-Weinberg principle, when the population is in equilibrium, then we will have freq(AA)=$p^2$ for the AA homozygotes in the population, freq(aa)=$q^2$ for the aa homozygotes, and freq(Aa)=2pq for the heterozygotes.

The term "Ewens-Watterson test" refers to a statistical analysis to determine selection of a particular SNP in a population. The results are reported using the F index.

The term "linkage disequilibrium" refers to the non-random association in population genetics of alleles at two or more loci. Linkage disequilibrium describes a situation in which some combinations of alleles or genetic markers occur more or less frequently in a population than would be expected from a random formation of haplotypes from alleles based on their frequencies. Non-random associations between polymorphisms at different loci are measured by the degree of linkage disequilibrium.

The term "odds ratio" (OR) refers to the ratio of the frequency of the disease in individuals having a particular marker (allele or polymorphism) to the frequency of the disease in individuals without the marker (allele or polymorphism).

The term "logistic regression" refers to a statistical test among a dichotomous outcome variable and explanatory variables.

The term "interaction model" refers to a statistical test where one SNP modifies the odds ratio of another SNP, however produces no association independently. This modification can either improve or decrease the original odds ratio.

The term "child" refers to a person between birth and full growth. In general, a child refers to an individual who is seventeen (17) years old or younger, including an infant.

The term "Haploview" refers to a publicly available statistical program (http://www.broad.mit.edu/mpg/haploview), that was used to construct haplotypes. The program takes into account each SNP's linkage disequilibrium with other SNP's to create groups.

The term "HapMap" refers to an internet genome browser run by the International HapMap consortium (http://hapmap.ncbi.nlm.nih.gov/), that reports SNP information according the ethnicity.

The term "reduced risk" is synonymous to "decreased risk" and "protection." For purposes of this application, the term refers to a reduction in the probability for a child to be inflicted with a disease such as acute lymphoblastic leukemia ALL. Risk is assessed by the probability of an individual to be inflicted with the disease.

The present invention provides a panel of SNPs that indicate a reduced risk in developing childhood ALL in a child. In one embodiment, the present invention provides a genotyping method for assessing the presence of such panel of SNPs in a child. In one embodiment, the present invention provides a plurality of haplotype tagging SNPs. For example, the presence of the haplotype tagging SNP rs807212 indicates the absence of all three (3) known pathogenic SNPs (namely, C282Y (rs1800562)-associated with iron overload and childhood ALL, H63D (rs1799945)-associated with iron overload, and rs9366637-associated with iron overload). Similarly, the presence of haplotype tagging SNP rs198853 indicates the absence of all three (3) pathogenic SNPs. Accordingly, the presence of the haplotype tagging SNPs (e.g., rs807212 and rs198853) is indicative of a reduced risk for a child to develop childhood ALL.

Using linkage disequilibrium analysis, the present invention provides a panel of SNP that exhibit strong linkage (i.e., correlation coefficient ($r^2$)≥0.9) with rs807212. The panel includes rs9467664, rs2213284, rs2230655 and rs12346. Because these four (4) SNPs have a strong linkage with the haplotype tagging SNP, it is speculated that they would function similarly or identically to that of the haplotype tagging SNP. For purposes of this application, these SNPs (exhibiting strong linkage with a haplotype tagging SNP such as rs807212) will be classified as haplotype tagging SNPs. Altogether, the present invention provides the haplotype tagging SNPs of rs807212, rs198853, rs9467664, rs2213284, rs2230655 and rs12346.

In a preferred embodiment, the haplotype tagging SNP is rs807212.

Surprisingly, the haplotype tagging SNPs identified are present in specific region outside the HFE gene. The SNPs (e.g., H63D and C282Y) are present within the HFE gene which is located 5 Mb telomeric to HLA-A in the extended HLA class I region. The present invention provides the extended haplotype structure of the HFE gene spanning a 152 kb region. The 152 kb region starts with rs15810 and ends with rs198815 (See FIG. 3). HFE gene is contained within the 152 kb region, which contains nine (9) SNPs (i.e., from rs2794719 to rs707889) (See, FIG. 3). All of the nine (9) SNPs within the HFE gene have a correlation coefficient ($r^2$)<0.5, indicating a non-significant linkage disequilibrium between these variants and rs807212.

The 152 kb region also encompasses 5' region and 3' region outside of the HFE gene (i.e., 5' region starts at rs115810 and ends at rs807212; and 3' region begins at rs12346 and stops at rs198809) (See, FIG. 3). There is a total of twenty-nine (29) SNPs that are present in the 5' and 3' region of the 152 kb. Out of these SNPs, there are twenty-six (26) SNPs that have a correlation coefficient ($r^2$) of ≥0.8 (See, Table 6), indicating a significant linkage disequilibrium between these variants and rs807212.

Because the HFE gene is located within the extended HLA complex, the present inventors genotyped a HLA homozygous reference cell line panel to assign HFE region haplotypes unambiguously. HFE is believed to be subject to natural selection (Rochette et al., 1999; Toomajian et al., 2003) and the present invention explored this possibility using the genotype data generated. In light of the HFE region haplotype data, the present inventors re-evaluated the C282Y association originally reported in the case-control group from South Wales (UK). The present invention therefore surveyed the allelic variants within and flanking regions of the HFE gene spanning 152 kb.

In accordance with the present invention, one of a skilled artisan understands that SNPs have two alternative alleles, each corresponds to a nucleotide that may exist in the chromosome. Thus, a SNP is characterized by two nucleotides out of four (A, C, G, T). An example would be that a SNP has either allele C or allele T at a given position on each chromosome. This is shown as C>T or C/T. The more commonly occurring allele is shown first (in this case, it is C) and called the major, common or wild-type allele. The alternative allele that occurs less commonly instead of the common allele (in this case, it is T) is called minor, rare or variant allele. To avoid confusion, in this patent application, we adopted to use wild-type and variant allele to define the common and rare alleles. Since humans are diploid organisms meaning that each chromosome occurs in two copies, each individual has two alleles at a SNP. These alleles may be two copies of the same allele (CC or TT) or they may be different ones (CT). The CC, CT and TT are called genotypes. Among these CC and TT are characterized by having two copies of the same allele and are called homozygous genotypes. The genotype CT has different alleles on each chromosome and is a heterozygous genotype. Individuals bearing homozygote or heterozygote genotypes are called homozygote and heterozygote, respectively.

The present inventors discovered the haplotype tagging SNPs that by examining genotype frequencies of polymorphisms in 415 newborns as well as 52 family samples. The present invention is directed to a method for diagnosing if a child may be at a reduced risk of childhood acute lymphoblastic leukemia by characterizing a genetic mutation, comprising the steps of: (a) obtaining a biological sample in need of diagnosis for reduced risk of acute lymphoblastic leukemia from a child who is suspected of affliction with the disease; and (b) assessing the presence of a haplotype tagging SNP selected from the group consisting of rs807212 and rs198853, wherein the presence of said haplotype tagging SNP is an indicator of a reduced risk (i.e., protection against) of childhood ALL in said child. Preferably, the haplotype tagging SNP is rs807212.

Because of the strong linkage disequilibrium (LD) ($r^2 \geq 0.9$), four (4) SNPs (i.e., rs9467664, rs2213284, rs2230655 and rs12346) occur on the same haplotype as rs807212. The present invention is also directed to a method for diagnosing, comprising the steps of: (a) obtaining a biological sample in need of diagnosis for reduced risk of acute lymphoblastic leukemia from a child that is suspected of afflicted with the disease; and (b) assessing the presence of a SNP selected from the group consisting of rs9467664, rs2213284, rs2230655 and rs12346, wherein the presence of said SNP is an indicator of a reduced risk (i.e., protection against) of childhood. ALL in said child.

In carrying out the methods of the invention, a biological sample is provided which includes DNA containing target nucleotide sequences (i.e., a mutated gene sequence is used as the target olignucleotide) derived from a human; typically, a child. Thus, the DNA useful, especially as target DNA, in the processes disclosed herein includes genomic DNA and the like. DNA is derived from a child.

By way of example, biological samples may be obtained from peripheral blood using well known techniques. In fetal testing, a biological sample is preferably obtained by cord blood sampling. An alternative source of biological sample may include buccal cells, bone marrow cells, and the like.

DNA is extracted from the biological sample using standard procedures, e.g., phenol:chloroform extraction as described by Maniatis et al., the disclosure of which is incorporated by reference. Other alternative procedures include commercially available genomic DNA extraction kits such as Qiagen (Valencia, Calif.).

In light of the foregoing, it is apparent that the present invention relates to diagnosis of leukemia diseases (exemplified by acute lymphoblastic leukemia (ALL)) caused by, induced by, or related to a genetic mutation in a region located outside of the HFE gene whose expression is affected by such mutation.

In one embodiment, the present invention provides a method of using genotype data rather than sequence data, SNPs are identified to support the findings in the association study. Hardy-Weinberg equilibrium (HWE) and Ewens-Watterson (E-W) tests are used in the present genotype-based tools to search evidence for selection.

HWE tests check the agreement between observed genotype frequencies and expected frequencies calculated from observed allele frequencies. A perfect agreement is expected when several assumptions are met. One of the assumptions is the absence of selection. A statistically significant result in the goodness-of-fit test examining the agreement suggests disequilibrium. The cause for this is change in genotype distribution in the population is usually selection. In practice, however, the most common cause for Hardy-Weinberg disequilibrium is genotyping errors. It is often possible to distinguish between selection and genotyping error when HWE is violated. Genotyping errors are unlikely to be selective.

In one embodiment, the present invention provides a method of using a statistical test (e.g., HWE) to verify the accuracy of the genotyping assay by analyzing the evolutionary selection for the population. The present invention also provides other statistical tests (e.g., E-W test) to complement the HWE test. One of ordinary skill in the art would recognize that detail of the HWE test is publicly available in Haploview version 4.0 (http://www.broad.mit.edu/mpg/haploview).

In one embodiment, the present invention provides another statistical test (i.e., E-W test) that can be used when population genetic data is available. E-W test shares some common feature as that of HWE test. When the E-W test attains a statistical significance, it is an indication of selection. Besides association tests, the present inventors tested the data with both HWE and E-W tests in order to obtain additional evidence for evolutionary selection in genotype data generated from a child. For the E-W test, a publicly available PopGen software version 1.32 (http://www.ualberta.ca/~fyeh) is used.

In accordance with the present invention, there is disclosed an optimal approach that utilizes genotyping to provide direct evidence for determining the allele variants of the haplotype tagging SNPs.

In one embodiment, the present invention provides a method of utilizing a haplotype tagging SNP to predict susceptibility to ALL in a child. In accordance with the present invention, the assessing techniques to determine the presence of a SNP are known in the field of molecular genetics. Further, many of the methods involve amplification of nucleic acids. (See, PCR Technology: Principles and Applications for DNA Amplification (Ed. H. A. Erlich, Freeman Press, NY, N.Y., 1992), and Current Protocols in Molecular Biology, Ausubel, 1999).

In one embodiment, the detection of the presence of a SNP in a particular gene is genotyping. Suitable genotyping procedures includes TaqMan allelic discrimination assay. In this assay, one may utilize an oligonucleotide probe labeled with a fluorescent reporter dye at the 5' end of the probe and a quencher dye at the 3' end of the probe. The proximity of the quencher to the intact probe maintains a low fluorescence for the reporter. During the PCR reaction, the 5' nuclease activity of DNA polymerase cleaves the probe, and separates the dye and quencher. Thus resulting in an increase in fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

Genotyping is performed using oligonucleotide primers and probes. Oligonucleotides may be synthesized and prepared by any suitable methods (such as chemical synthesis), which are known in the art. Oligonucleotides may also be conveniently available through commercial sources. One of the skilled artisans would easily optimize and identify primers flanking the gene of interest in a PCR reaction. Commercially available primers may be used to amplify a particular gene of interest for a particular SNP. A number of computer programs (e.g., Primer-Express) is readily available to design optimal primer/probe sets. It will be apparent to one of skill in the art that the primers and probes based on the nucleic acid information provided (or publicly available with accession numbers) can be prepared accordingly.

The labeling of probes is known in the art. The labeled probes are used to hybridize within the amplified region during the amplification region. The probes are modified so as to avoid them from acting as primers for amplification. The detection probe is labeled with two fluorescent dyes, one capable of quenching the fluorescence of the other dye. One dye is attached to the 5' terminus of the probe and the other is attached to an internal site, so that quenching occurs when the probe is in a non-hybridized state.

Determination of the presence of a particular SNP is typically performed by analyzing a nucleic acid sample present in a biological sample obtained from an individual. Biological sample is derived from a child and the nucleic acid sample comprises genomic DNA. The nucleic acid may be isolated from blood samples, cells or tissues. Protocols for isolation of nucleic acid are known.

In another embodiment, the genotyping procedure includes PCR-RFLP. PCR-RFLP represents an alternative genotyping method used in the invention. PCR-RFLP can yield unambiguous results provided that there is a suitable endonuclease that will cut the amplified PCR product containing a SNP if it contains one of the alternative nucleotides but not the others. Results of PCR-RFLP may be achieved by visualization of fragments on a gel following restriction endonuclease digestion of the PCR product. Thus, a fragment of DNA containing the SNP is first amplified using two oligonucleotides (primers) and is subject to digestion by the variant allele-specific restriction endonuclease enzyme. If the fragment contains the variant allele it is cut into two or more pieces and in the absence of the variant allele, the PCR product remains intact. By visualizing the end-products of the digestion process by agarose or polyacrylamide gel electrophoresis, the presence or absence of the variant allele is easily detected. Other suitable methods that are known in the art such as single-base extension assay, oligonucleotide ligation assay, DNA microarray, pyrosequencing, high-resolution melting method, denaturing high-performance liquid chromatography, mass spectrometry, microsphere-based suspension array platform (Luminex)-based assays and the like can be used in the present invention to detect the presence of SNP.

In yet another embodiment, the genotype procedure includes high resolution melting assay (HRM). HRM can provide results if there is a suitable probe specific to the region studied and can bind to the variant sequence well. Results of HRM may be achieved by visualization of the fluorescent melt profile on a high resolution scanner. Thus, a fragment of DNA containing the SNP is first amplified using two oligonucleotides (primers) where one oligonucleotide is added in excess. The PCR product is heated up and allowed to hybridize with the variant-specific probe. Free fluorophores (e.g., SYBR green and the like) bind to the product-probe hybrid and begin to fluoresce. Once the primer-probe complex is formed, it is slowly heated (e.g., to 100° C.) to denature the primer-probe complex. Then the fluorescence is removed. If the product contains the variant allele, it will have a higher denaturation temperature and the rate of loss of fluorescence versus temperature will be higher. However, in the absence of the variant allele, the probe quickly denatures, producing a lower loss of fluorescence versus temperature. By visualizing the fluorescence profiles, one of ordinary skill in the art would easily detect the presence of the variant allele (e.g., C282Y rs1800562).

As appreciated by one of skill in the art, other suitable genotyping assays may be used in the present invention. This includes hybridization using allele-specific oligonucleotides, primer extension, allele-specific ligation, sequencing, electrophoretic separation techniques, and the like. Exemplary assays include 5' nuclease assays, molecular beacon allele-specific oligonucleotide assays, and SNP scoring by real-time pyrophosphate sequences.

Additional suitable methods may also be employed in SNP detection. These methods include single-base extension assay, oligonucleotide ligation assay, DNA microarray, pyrosequencing, denaturing high-performance liquid chromatography, mass spectrometry, microsphere-based suspension array platform (Luminex)-based assays and the like. All of these methodologies are well known in the art and one skilled artisan would easily optimize these assays in order detect the presence of SNPs in accordance with the present invention.

In one embodiment, the present invention provides a panel of SNPs that are useful in predicting risk for childhood ALL. This panel of SNPs includes rs807212, rs198853, rs9467664, rs2213284, rs2230655 and rs12346. Preferably, the SNP is the haplotype tagging SNP rs807212, rs198853. More preferably, the SNP is the haplotype tagging SNP rs807212.

In another embodiment, the present invention provides a method of utilizing multiple SNPs that would exert joint effects and alter the individual's susceptibility to childhood ALL in a child.

In one embodiment, the present invention provides a method of using haplotype tagging SNPs (i.e., htSNPs). htSNPs represent a cluster of SNPs in their vicinity; together, they provide additional information about genetic variation. The present invention provides a method of using the htSNP approach. When there is no already known functional SNP available in a candidate gene, the present invention provides a method of using htSNPs to predict individual's susceptibility to childhood ALL. The goal is to use functional SNPs that are known to affect either the function or expression of a gene. The use of functional SNPs may yield a positive association. On the other hand, a non-functional SNP may also be a marker to predict the outcome.

Haplotype tagging SNPs are capable of representing other SNPs. This is because of a phenomenon called linkage disequilibrium (LD). An htSNP and other SNPs tagged or represented by the htSNP form a group that are equally informative when genotyped individually. Any pair of SNPs that are in linkage disequilibrium may provide the same information. If one SNP is associated with a disease condition, the other SNP is similarly associated with the same disease condition. This generates a situation in genetic association studies where an association may be replicated by using a different SNP that is in the linkage disequilibrium with the original SNP. Accordingly, the SNPs in the present panel may be replaced by other SNPs to yield the same information. The linkage disequilibrium information is available in public resources such as HapMap (http://www.hapmap.org) or genome variation server (GVS: http://gvs.gs.washington.edu/GVS).

In accordance with the present invention, the present inventors searched for a novel SNP marker that bears high correlation with leukemia, in particular childhood ALL. Comprehensive analysis of the region spanning 152 kb including the HFE region was conducted using haplotype construction. The haplotype construction was based on using: (i) population samples, (ii) homozygous cell line panel, and (iii) HapMap and Haploview analytical software from publicly available sources. The haplotype construction of the 152 kb region includes the analysis of neighboring histone genes. This combined approach identifies the presence of two (2) haplotype tagging SNPs (i.e., rs807212 and rs198853). The presence of these haplotype tagging SNPs (i.e., either rs807212 or rs198853) is indicative of the absence of three (3) pathogenic SNPs (i.e., C282Y (rs1800562), H63D (rs1799945), and rs9366637), all of which represent variants that are known to increase the risk for childhood ALL as well as high iron levels (see, Table 1). Accordingly, the present finding indicates both rs807212 and rs198853 can serve as an accurate and reliable genetic marker to predict a reduced risk of childhood ALL in a child.

The identification of the presence of haplotype tagging SNPs located outside the HFE gene is surprising. Earlier findings support three (3) pathogenic SNPs presence within the HFE gene. C282Y (rs1800562) is shown to be associated with childhood ALL in Welsh population. H63D and rs9366637, both also present within the HFE gene, are associated with iron overload. If there exists a haplotype tagging SNP, one would expect its presence to be within the HFE gene. To the contrary, we identified two (2) haplotype tagging SNPs, both are located within the histone genes found in the histone island on Chromosome 6 (i.e., their location is outside of the HFE gene).

Further haplotype analysis using HapMap data has enabled us to identify at least twenty six (26) SNPs having linkage disequilibrium (LD) with the haplotype tagging SNP rs807212 (See, Table 6). The twenty six (26) SNPs that are scattered along the 152 kb region surrounding the HFE gene exhibit a strong linkage disequilibrium (LD) among themselves (i.e., correlation coefficient $(r^2) \geq 0.8$), but not with any HFE SNPs (i.e., correlation coefficient $(r^2) < 8$). Among these twenty six (26) SNPs, we identified four (4) SNPs that exhibit strong linkage disequilibrium (LD) (i.e., correlation coefficient $(r^2) \geq 0.9$) with the haplotype tagging SNP rs807212. They include rs9467664, rs2213284, rs2230655 and rs12346, all are found to be outside of the HFE gene (i.e., histone region on Chromosome 6). This finding is consistent with the hypothesis that HFE gene is inserted into the histone gene island in the genome during evolution. It is of interest to note that the location between HFE and histone genes is identical in mice as in human.

Some variants withing haplotype shows signs of natural selection by Ewens-Watterson analysis of the control data (Table 4). It further suggest that the selection is driven by the 152 kb region but not necessarily driven by the HFE gene itself as had been proposed by Rochette et al. (1999) and Toomajian et al. (2003). Notably, despite that the C282Y is not present in both Asian and African population samples, the selection still persists in these two population samples (See, Table 7). Therefore, it is concluded that the selection is driven by the histone gene regions outside of the HFE gene.

As shown in Table 5, most of the twenty six (26) SNPs had similar variant allele frequencies in European and African population samples. This observation suggests a possible common origin for this cluster of SNPs. They may represent segmental duplications in this part of the genome containing the 55 histone genes. The present inventors have identified a cluster of twenty six (26) SNPs on either side of the HFE gene that are in strong linkage disequilibrium (LD) (correlation coefficient $(r^2) \geq 0.8$) with similar variant allele frequencies. The SNP rs807212 tagging of these twenty six (26) SNPs (hence the name haplotype tagging SNP).

The present invention provides rs807212 as a reliable marker for the most frequent HFE haplotype. Because the presence of rs807212 indicates the wild-type of C282Y (i.e., absence of the C282Y SNP), the rs807212 is a marker for a reduced risk in childhood ALL.

Besides C282Y, we further identified a haplotypic relationship of the rs807212 variant with two (2) other SNPs present in the HFE gene (i.e., H63D (rs1799945) and rs9366637). The presence of intergenic variant rs807212 marks these two (2) wild-type alleles at the HFE gene variants of H63D, rs9366637. Because these two (2) HFE SNPs are also pathogenic, the presence of rs807212 indicates a reduced risk for childhood ALL.

Because rs9467664, rs2213284, rs2230655 and rs12346 are shown to have a strong linkage disequilibrium (LD) correlation coefficient $(r^2 \geq 0.9)$, with the haplotype tagging SNP rs807212, they also represent a reliable genetic marker for reduced risk of childhood ALL. Whether the protection conferred by these SNPs (such as rs807212) are due to the lack of HFE variants and influencing iron levels or due to a direct effect of the histone gene variants is presently unclear. It is possible that a combination of these SNPs is responsible for the protection observed in the present study.

Notably, among the twenty-six SNPs present within the 152 kb region on Chromosome 6, four (4) SNP (i.e., rs9467664, rs2213284, rs2230655 and rs12346) have a correlation coefficient of $\geq 0.9$. The remaining twenty-two (22) SNP all possess a correlation coefficient of $\geq 0.8$ but $<0.9$. For purposes of the present invention, a SNP that has a correlation coefficient of $\geq 0.9$ represents a more reliable substitute for the haplotype tagging SNP rs807212, than that which has a correlation coefficient of $<0.9$. Accordingly, the four (4) SNPs can serve as (similar to the haplotype tagging SNP rs807212) a reliable indicator for a reduced risk in childhood ALL.

EXPERIMENTAL STUDIES

Example 1

Homozygous Cell Line Panel

We obtained from International Histocompatability Working Group (IHWG) a panel of human cell line (a total of eight-two (82) cell lines), all exhibiting homozygosity with respect to the HLA region on Chromosome 6. DNA from these cell lines were obtained by extraction protocol using standard phenol-chloroform procedure. The HLA homozygous cell lines (n=82) were genotyped for alleles at the respective loci spanning a 52 kb region (gene region spanning rs8384 to rs198844) which includes the HFE gene (See, Table 1). Specifically, we genotyped twenty-five (25) SNPs that are present within the 52 kb region (Table 2). Fifty (50) homozygous cell lines (out of eight-two (82)) were found to exhibit homozygosity at all of the twenty-five (25) SNP sites.

We constructed the haplotypes and determined the frequency of these haplotype structures within these cell lines (See, Table 1). Haplotype 1, as marked by rs807212, is the most frequent occurring (i.e., frequency=0.283) haplotype in our tested human cell lines. Unlike C282Y and H63D (both were found to be non-variant), rs807212 represents the variant allele for haplotype 1. We concluded, therefore, that variant allele rs807212 is the haplotype tagging SNP for haplotype 1. The presence of the rs807212 indicates a protection from childhood ALL because the presence of rs807212 implies the absence of C282Y and H63D.

Haplotype 7 has a frequency of 0.045 that corroborated the European population frequency. Haplotype 7 as marked by C282Y was found to appear in two cell lines (i.e., IHWG numbers WT100BIS and H0301) (Table 1).

In an independent series of study, we genotyped additional SNPs (all of the tested SNP loci are listed in Table 2). However, we have only genotype these SNPs in the cell line panel. For example, we genotyped the SNPs rs9467664, rs2213284, rs2230655, rs4529296, rs2794719, rs1800730 and rs12346 in the cell line panel. Of these, SNPs rs9467664, rs2213284, rs2230655 and rs12346 were genotyped because of their strong relationship with rs807212 (see below; Linkage Disequilibrium) and these four (4) SNPs had identical genotypic results as that of rs807212 (Table 2). Therefore, like rs807212, these four (4) SNPs can serve as haplotype tagging SNP for haplotype 1.

Example 2

Genotyping Population Samples

A total of 532 clinical samples were obtained from newborns in South Wales (UK) (representing European population). The clinical sample analyzed in this study was the anonymously collected cord blood samples from newborns. In this group of 531 samples, there were 117 childhood acute lymphoblastic leukemia (ALL) samples (64 males and 53 females) diagnosed in South Wales consecutively during a ten-year period. There were 414 control samples from contemporary subjects who were diagnosed free of childhood ALL.

DNAs were extracted from core blood samples of these two groups and subjected to the same genotypic analysis as mentioned in Example 1.

The haplotype analysis showed unambiguously that the haplotype structures found in the clinical samples agreed to that found in the homozygous cell lines (Table 1). The most common haplotype in the population sample is haplotype 1 having a frequency of 0.283. The same haplotype 1 occurred in 11 homozygous cell lines (out of the 50 homozygous cell lines) (Table 1).

Also shown in Table 1 is the panel of SNPs (i.e., a total of 19) that were used to construct the haplotype. Notably, the variant alleles of rs807212 and rs198853 are found only on haplotype 1 (and not on haplotypes 2-11) (See, Table 1). Both rs807212 and rs198853 can serve as haplotype tagging SNP for haplotype 1.

C282Y and H63D loci have been previously documented to have association with childhood ALL. In other words, the presence of the variant alleles at these two loci increases the risk of childhood ALL. Our haplotype analysis, however, showed that C282Y and H63D loci are absent on haplotype 1 (Table 1). Because these two loci are associated with increased ALL risk, their absence of the C282Y and H63D variant alleles indicate that haplotype 1 is protective of childhood ALL.

The haplotype construction in the population sample as supported by the data from both the cell lines showed that four (4) haplotypes were tagged by single SNPs (Table 1). First, variant allele of rs807212 exclusively occurred on haplotype 1. Second, variant allele of rs1759679 occurred on haplotype 5. Third, variant alleles of rs9366637/rs9393682/rs2050947 occurred on haplotype 6. Fourth, variant allele of rs1800562 (C282Y) occurred on haplotype 7. This observation has significant implications in the interpretation of association tests because SNP rs1800562 (on haplotype 7) has been associated with iron overload and leukemia in patients. Variant allele rs9366637 (on haplotype 6) has also been associated with large birth weight.

As shown in Table 1, the HFE intron 1 SNP rs9366637 and the intergenic region SNPs rs9393682 and rs2050947 that exclusively occur on haplotype 6 have a frequency of less than 0.10 in Europeans and Africans, but the same allele is the major allele in Chinese and Japanese populations. Out of 11 cell lines whose origins are listed as Asian, Japanese, Chinese or Amerindian in the IHWG database (Table 5), 10 were positive for the rs9366637 minor allele.

As shown in Table 1, H63D, the older of the two disease-causing mutations of the HFE gene, occurred on haplotypes 4 and 8. These two haplotypes were identical for the variants within and centromeric to HFE and the differences were in 5' flanking region SNPs. The previously reported linkage disequilibrium between H63D and HLA-A29 in the Portuguese population (Cardoso et al, 2002) appeared to be exclusive to haplotype 8.

Example 3

Newborn Population Sample

Hardy-Weinberg equilibrium (HWE) in control subjects yielded significant deviations at the intergenic region SNP rs807212, HFE 3' region SNP rs12346 and HFE intron 5 SNP rs2858996 (P<0.001; Table 3). We included the intron 5 SNP, rs2858996, in our analysis, but it did not contribute to haplotype construction, population genetics findings or associations with leukemia. The analysis of rs807212 and rs12346 in the case-control set suggested strong associations and the genotyping of these SNPs were repeated by PCR-RFLP methods. The RFLP results were in HWE and they were used for the subsequent analyses. There were statistically insignificant deviations in four other SNPs (rs8384, rs1799945, rs707889, rs17596719) as shown in Table 3. All deviations were statistically significant only in female newborn controls, but not in males.

Variant allele frequencies of each variant in the samples from Welsh population were similar to European frequencies found in the HapMap project (Table 2). The SNP rs807212 which tagged the most common haplotype (Table 1), had a lower frequency in the Welsh sample compared with the HapMap sample (0.323 vs 0.358, respectively). The C282Y frequency has previously been reported to be higher in the Welsh population (Distante et al., 2004).

Because our main goal was to explore the C282Y association, we examined linkage disequilibrium (LD) between each SNP and C282Y (Table 3) to identify evidence for confounding by locus. Several SNPs showed positive LD with C282Y, but none of the SNPs explained the C282Y association with leukemia.

Figure 2:
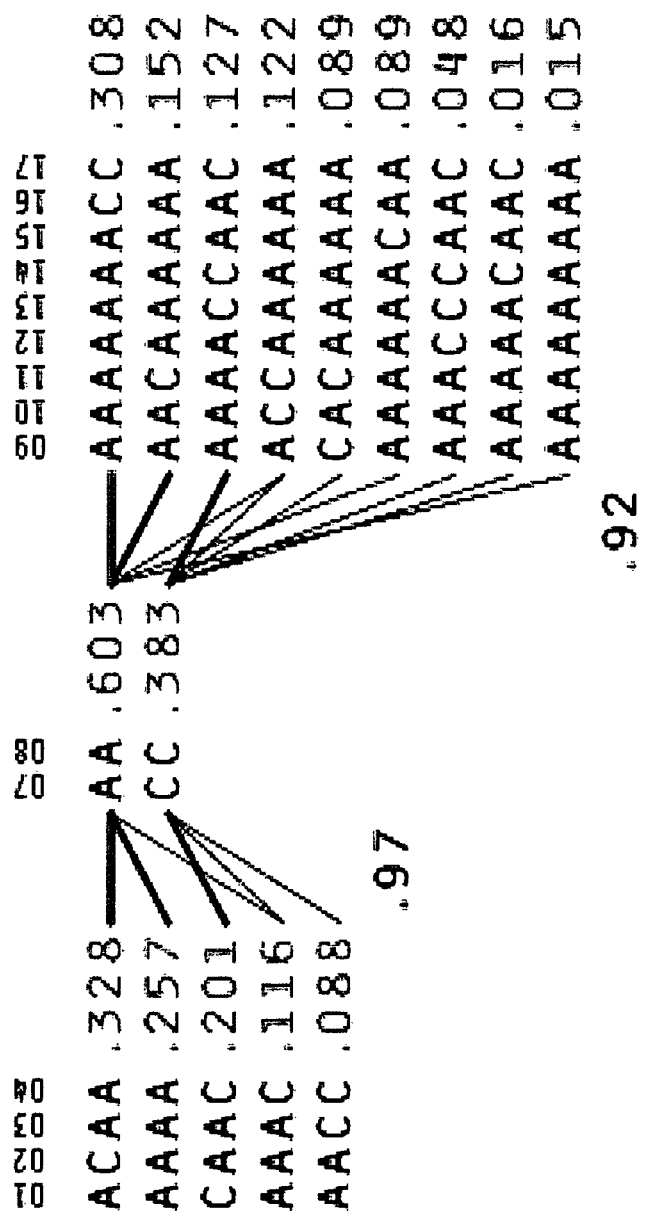
FIG. 2 depicts frequencies of each of the three (3) haplotype blocks as shown in FIG. 1. SNPs listed in FIG. 1 and Table 1 were given positional numbers and are represented by their positional number in FIG. 2. For example, rs8384 is given the positional number of 01. The letter "A" represents the wild-type of the locus. The letter 'C'denotes the variant allele of the locus. However, with respect to the SNP No. 16(i.e., rs198853 present in histoneH1T gene), the variant allele occurs more frequent in European than that of the wild-type and is coded as 'A'. The correlation coefficient between block 1 and block 2 is 0.97. The correlation coefficient between block 2 and block 3 is 0.92. Haplotype block frequencies as determined on Haploview in controls (SNP numbers are as given in Table 2 and FIG. 1a; '2' denotes minor allele, however, for HIST1H1T SNP, allele G, which is in LD with C282Y and no longer the minor allele in Europeans is coded as 2; note that the 5' flanking region SNP rs807212 does not belong to haplotype block 1 and is not represented in haplotypes).

Using an interaction model, we found no difference in sex-specific LD patterns in controls. The LD plot with haplotype blocks and frequencies in control subjects were summarized in FIGS. 1 and 2, respectively. One notable observation was that LD between rs807212 and rs10425 (D'=0.84; $r^2$=0.684) was smaller as that observed in the HapMap data (D'=1.0; $r^2$=0.894; see below). Frequencies of the HFE region haplotypes in the control group containing all SNPs analyzed in the present study were obtained by forcing Haploview to treat the whole region as a haplotype block by using the solid spine option (Table 1).

The most common haplotype in the population sample (Table 1) was tagged by rs807212. This haplotype was characterized by the wild-type alleles of the HFE mutations H63D and C282Y as well as the intron 1 variant rs9366637, which has been reported to influence birth weight and childhood ALL risk (Dorak et al., 2007). Although no haplotype showed statistically significant frequency differences between male and female newborns, haplotype 1 frequency was slightly higher in male newborns (0.305 vs 0.265).

The statistically non-significant male-female difference in the frequency of haplotype 1 tagged by rs807212 prompted us to consider a possible selection event on rs807212. Bioinformatics analysis presented below showed that in HapMap data, rs807212 and other SNPs in strong LD with it had heterozygote excess. We examined the heterozygosity rates in our data. There was a statistically non-significant increase in heterozygosity (0.455 vs expected value of 0.438), unlike the extreme excess in HapMap data (0.583 vs 0.460). The corresponding F index was −0.0392 (quantitating heterozygote excess) with no difference between males and females.

Example 4

Pedigrees from Northern Ireland

In this series of study, we examined the potential haplotypic relationship between the haplotype tagging SNP (i.e., rs807212) and HFE gene mutations. As shown in this study, rs807212 serves as a protective SNP marker and is a haplotype tagging SNP. HFE is the gene that causes iron overload disorder associated with leukemia (e.g., childhood ALL). The HFE gene spans rs2794719 to rs707889 and includes rs1800562 (C282Y) and rs179945 (H63D) (See, Table 2). Mutation within the HFE is quite common, especially C282Y. C282Y is believed to be a risk marker for childhood ALL, although other HFE mutations may modify the leukemia risk.

We have obtained 272 clinical samples from 52 families who were originated from Northern Ireland. DNA was extracted from these clinical samples and we genotyped these clinical samples for nineteen (19) SNPs surrounding the HFE gene. These SNPs start from rs8384 to rs198844 as listed in Table 1. Because minimal chromosome recombination may occur between two generations, we took advantage of this fact to determine haplotype structure among the 52 family members and to assess chromosomal distribution between generations of these 52 families. To do so, we constructed the haplotypes with these families and compared the result to the haplotype structures of the Welsh samples and the homozygous cell line.

We confirmed the haplotypic relationship between rs807212 and HFE mutations H63D and C282Y in the 272 samples from the 52 families. The rs807212 variant allele was not present on the same haplotype as the C282Y and H63D variants. Therefore, homozygosity for the rs807212 variant allele represents the wild-type HFE genotype (i.e., lacking the C282Y and H63D variants) and is a protective marker against childhood ALL.

Example 5

HapMap and HaploPlotter Data

The rs807212 is intergenic and has no known functionality attributed to this SNP. We employed HapMap to determine if the rs807212 tags a functional SNP in its vicinity. Table 6 depicts a set of twenty-six (26) SNPs which spans 152 kb from rs115810 (nucleotide position: 26 083 862; TRIM38) to rs198815 (nucleotide position: 26 235 250; centromeric to HIST1H1T).

The 26 SNPs as determined by HapMap analysis maintained rs807212 as their haplotype tagging SNP (Table 6). We further performed statistical analysis to confirm this finding. Pairwise LD parameters among these 26 SNPs scattered along the histone gene island were D'=1.0 and r2>0.8 (mean $r^2$ of 0.915; see Table 6). The 152 kb block covers the telomeric half of the histone gene cluster on Chromosome 6p.

In the present study, seven (7) of the 26 SNPs were genotyped in the cell line panel (from telomere: rs9467664, rs2213284, rs2230655, rs10425, rs807212, rs12346, rs198853). With the exception of rs10425, which had the lowest $r^2$ value with rs807212 (Table 6), identical genotypes were revealed in the 82 cell line samples. Exploration of the PERLEGEN database through GVS identified an additional SNP that is not included in the HapMap project (rs1150660). This SNP has an $r^2$ value of 0.96 with rs807212. An intriguing observation in the HapMap data was that for most of these 26 SNPs, the P values for HWE were close to statistical significance (Table 6). The SNPs that were most strongly linked with each other ($r^2$>0.90) in this block had P values for HWE of less than 0.10, suggesting genotyping errors or selection.

To further explore the meaning of the selection signal provided by rs198844 in our data, we performed Haploplotter analysis (using the HapMap data). When the HFE gene and 5 Mb downstream and upstream regions were selected for analysis, there was statistically significant selection acting on the segment telomeric to HFE extending to SLC17A2/TRIM38 (nucleotide positions 26 020 961 through 26 205 038; see Table 7). There was marginally significant selection at neighboring genes, including HIST1H1T. This segment almost perfectly corresponded to the cluster of SNPs that are in tight LD and tagging the most common haplotype in the HFE region. The selection was evident not just in the European sample, but also in the Asian and African samples.

Example 6

Associations in Childhood ALL

So far, we have obtained detailed information on the haplotype structure of the HFE region. In this next series of study, we re-evaluated the HFE associations in the original case-control set, which showed the C282Y association. This case-control sample does not have sufficient statistical power for analysis of all adjusted associations and interactions. The results of multivariable analyses, therefore, need to be considered preliminary. Table 8 summarizes all association statistics.

When we examined the adjusted HWE P values (PHWE), which assesses HWE in cases after normalization for genotype frequencies in controls, the most extreme deviation from HWE in cases was at rs807212 suggesting a possible association. The sex-specific minor allele frequencies of this SNP showed statistically non-significant differences in opposite direction in cases and controls. The male-specific protection conferred by rs807212 from childhood ALL was the strongest association (Table 8). This SNP tags haplotype 1 that contain the wild-type alleles of the HFE variants known to increase cancer risk. Other associations observed were protection by rs10425, risk by C282Y and risk by rs17596719. All of these associations were either exclusive to or stronger in males and resulted from their haplotypic relationships with rs807212 and secondary to the rs807212 association.

Example 7 rs807212 Association

There was a difference in allele frequencies between cases and controls which originated exclusively from males (0.167 in cases and 0.343 in controls; P<0.001). The additive model for this SNP showed a strong protective association (per allele OR=0.55; P=0.001) with childhood ALL, which was male-specific (per allele OR=0.38; P<0.001) and not statistically significant in females (P=0.42).

Using wild-type genotype as a reference, the risk reduction increased stepwise from heterozygosity (OR=0.35; P=0.001) to homozygosity (OR=0.18; P=0.03) for the minor allele in males. For the association with the minor allele homozygosity, there was an interaction with sex because of an opposite trend in females (P for interaction=0.04). While the additive model was statistically significant only in males, heterozygote advantage was evident in both sexes. Heterozygosity conferred protection from childhood ALL (OR=0.43, 95% CI=0.27 to 0.69; P<0.001), which was statistically significant in both males (P=0.007) and females (P=0.02).

The most common haplotype of the HFE region (haplotype 1) harbors the rs807212 minor allele and neither C282Y nor H63D mutations of HFE. Statistical analyses suggested that associations with other haplotypes that lack the rs807212 minor allele were secondary to lacking the protective effect of rs807212.

We next examined the opposite to see whether the rs807212 protective association was entirely independent. Statistical adjustment suggested a reciprocal relationship. When the rs807212 association was assessed after stratification for the C282Y and H63D mutation status, the protective association got weaker and statistically non-significant (per allele OR (additive model)=0.80; P=0.53). The observed association with rs807212 was due to its being a marker for wildtype HFE haplotype that lacks HFE mutations C282Y and H63D and possibly other unknown sequence variants within the HFE gene. We did not have sufficient statistical power to conclusively exclude a residual protective effect of rs807212, perhaps as a marker of a large histone cluster haplotype besides the protective effect it shows as a marker of the wildtype HFE haplotype.

Example 8

Haplotype Analysis

We performed a Haploview analysis on complete haplotypes. The results showed a frequency difference between cases and controls for haplotype 1 (tagged by rs807212; 0.195 vs 0.284; P=0.01). This difference was due to the difference between male cases and controls (0.154 vs 0.305; P=0.002).

EXPERIMENTAL PROTOCOLS

I. Materials (i) Reference Cell Line Samples

International Histocompatibility Working Group (IHWG) reference cell line DNA samples representing a variety of ethnicities were genotyped for all 24 variants. Eighty-two (82_DNA samples of HLA-typed cell lines were obtained from International Cell and Gene Bank (Seattle, Wash.). It was anticipated that the homozygosity at the HLA complex in most of these samples would extend through the HFE gene in the extended HLA class I region. Only those homozygous at the HFE region (n=50) were used to construct the HFE region haplotypes. A complete list of cell line samples genotyped is provided in Table 5.

(ii) Population Samples

The sample of a European population analyzed in this study was the anonymously collected cord blood samples from newborns in South Wales. The characteristics of this sample have been described elsewhere (Dorak et al., 2002). The cases analyzed in the original association study were 117 childhood ALL samples (64 males and 53 females) diagnosed in South Wales (U.K.) consecutively during a ten-year period and originally used to describe the male-specific C282Y association (Dorak et al., 1999).

The family samples were from Northern Ireland and have been described elsewhere (Middleton et al., 2007). For the current analysis, there was sufficient DNA from fifty-two (52) families out of the original seventy-seven (77) families included in recruitment. A total of 272 samples from these families, each one with both parents and up to eleven (11) children, were included in selected genotypings for confirmation of haplotypic relationships. Local research ethics committees provided favorable opinion for the use of these samples in population genetic studies.

II. SNP Selection

The C282Y mutation (rs1800562) was already typed in the case-control group by PCR-RFLP (Dorak et al., 1999) but was retyped by a high resolution melting (HRM) analysis (see below). The second most frequent mutation (H63D) was also included and genotyped by HRM. For additional SNP selection, we used the online resource FastSNP (Yuan et al., 2006) to pick functionally relevant variants. FastSNP was also used to assess effects of variants in silico. Haplotype tagging SNPs (htSNP) were selected using HapMap project data (release 20/phase II; http://www.hapmap.org). We aimed to cover the HFE gene, flanking intergenic regions and neighboring histone genes. The characteristics of the 24 HFE region SNPs analyzed are shown in Table 2.

III. Genotyping Procedures

A) Allelic Discrimination Assays

TaqMan allelic discrimination assay utilizes an oligonucleotide probe labeled with a fluorescent reporter dye at the 5' end of the probe and a quencher dye at the 3' end of the probe. The proximity of the quencher to the reporter in the intact probe maintains a reduced fluorescence for the reporter. During the PCR reaction, the 5' nuclease activity of DNA polymerase cleaves the probe, thereby separating the reporter dye and the quencher dye and resulting in increased fluorescence of the reporter. Accumulation of PCR product is detected directly by monitoring the increase in fluorescence of the reporter dye. The 5' nuclease activity of DNA polymerase cleaves the probe between the reporter and the quencher only if the probe hybridizes to the target and is amplified during PCR. The probe is designed to straddle a target SNP position and hybridize to the nucleic acid molecule only if a particular SNP allele is present.

TaqMan allelic discrimination assays were performed on Stratagene MX3000P instruments. The standard thermal profile protocol was used with the modification of 90 seconds at 60° C. for 50 cycles. TaqMan® SNP genotyping assays purchased from ABI as 40× were diluted to 20× by adding Tris-HCl and EDTA at pH 8.0. 96-well plates were set up by adding 1.5 µl DNA (10 ng/µl), 4.625 µl ddH$_2$O and 6.25 µl TaqMan® genotyping master mix (ABI) and 0.625 µl assay reagents. Each plate contained intra and inter-plate controls and no-template controls. Built-in Stratagene Mx3000P software was used to assign genotypes.

TaqMan allelic discrimination assay was used to genotype all SNPs except rs807212, H63D, S65C, C282Y, rs12346 and rs2794720. The standard Applied Biosystems (ABI, Foster City, Calif.) thermal profile protocol was used. TaqMan SNP genotyping assays were purchased from ABI. 96-well plates were set up using 10 ng genomic DNA. Each plate contained intra and inter-plate controls and no-template controls. Each SNP was analyzed in singleplex reactions. Allelic discrimination assays were performed on the Stratagene Mx3000P instrument.

B) SNP Variation Discrimination Using High Resolution Melting (HRM)

High resolution melting assay utilizes an unlabelled oligonucleotide probe with a dideoxy 3' end to prevent amplification. Primers are designed to flank the area in question and are added to the PCR reaction with the probe and free-floating fluorophores. The amplification process occurs asymmetrically; the strand that will hybridize to the probe is selectively amplified more than the complementing strand. The PCR products are then heated and cooled quickly to denature the double-stranded product and allow the probe to bind, while simultaneously allowing the fluorophore to bind to the probe-product heteroduplex. The sample is then loaded into a high resolution scanner that measures the fluorescence over temperature and heated to denature the heteroduplex. Since the probe is designed to bind tightly to the variant, it will have a higher melting temperature than the other allele and a longer fluorescent reading. The alleles are differentiated by their rate of fluorescence lost over temperature.

The HRM analysis was used to genotype H63D (rs1799945), S65C (rs1800730) and C282Y (rs1800562) using the Idaho Technology Light Scanner instrument as described by Thou et al (2004). Each asymmetric PCR reaction contained a final concentration of 1× LCGreen MasterMix (Idaho Technology Inc, Salt Lake City, Utah), 0.06 µM forward primer, 0.3 µM reverse primer, 0.24 µM probe (3' blocked), 10 ng genomic DNA and water to raise the final volume to 10 µl. HRM was also used to re-type C282Y (rs1800562) with slight modification of the reaction conditions (Thou et al., 2004). We also used HRM analysis to genotype the 5' flanking region SNP rs2794720 with the primers (5' to 3')

```
                                         (SEQ ID NO: 1)
    F:      TCTCAACCTTAGACCAACTTATGTCTT (0.5 µM);

(SEQ ID NO: 2)
    R:      CATTCTCCAGATAATCCCAATACT (0.1 µM);
    and
```

```
                                         (SEQ ID NO: 3)
    Probe   TACTGAAACACGTTCCACAGCC (0.4 µM).
```

The amplification program consisted of an initial denaturation phase at 94° C. followed by 45 cycles of 94° C. for 30 seconds, 64° C. for 30 seconds and 72° C. for 30 seconds, a final denaturation at 94° C. for 30 seconds and a rapid cooling to 28° C. for 30 seconds. The amplicons were melted on the LightScanner instrument from 55° C. to 90° C. and the results analyzed using the LightScanner Call-it software version 2.

C) Polymerase Chain Reaction-Restriction Fragment Length Polymorphism (PCR-RFLP) Analysis In these series of study, PCR-RFLP analysis was performed to genotype the intergenic SNP rs807212. In this analysis, oligonucleotides (5' to 3', F: CGAGAAGCGATG-GTCATTTT (SEQ ID NO: 4) and R: CCTTCATGGTGGT-GTTT GAA (SEQ ID NO: 5)) and the restriction endonuclease MspI were used. In the first step, using the oligonucleotides, a 198 bp fragment was amplified by PCR. PCR was done under standard conditions using 20 ng of genomic DNA and annealing temperature of 55° C. The fragments were then subjected to restriction endonuclease digestion by using the MspI enzyme. This enzyme cuts the fragment into two fragments of 108 bp and 90 bp when there is a C allele in the SNP position but fails to cut it when there is a T allele in the SNP position. Samples with only 108 bp and 90 bp fragments were classified as homozygote for allele C and samples with only the 198 bp fragment were classified as homozygote for allele T. Samples that contained 198 bp, 108 bp and 90 bp fragments were classified as heterozygote for alleles C and T.

All primers and probes were synthesized at Integrated DNA Technologies (IDT, Coralville, Iowa) and endonucleases (MspI) were purchased from New England BioLabs Inc. (Ipswich, Mass.).

IV. Data Analysis

The cell line data were analyzed manually to assign haplotypes in homozygous samples. The newborn group was analyzed on Haploview v4.0url: <broad.mit.edu/mpg/ haploview>) (Barrett et al., 2005), to construct haplotypes and to obtain an LD plot. Haploview was also used to evaluate allelic and haplotypic associations between cases and controls and to obtain haplotype frequencies. We used PopGene v1.32(url: <ualberta.ca/~fyeh/index>) to assess neutrality of each SNP by the Ewens-Watterson test as well as to obtain Wright's fixation index to determine heterozygote excess or deficiency. Comparison of allele frequencies and LD patterns was made using the existing European (CEU) data from the HapMap project. The SNP that showed evidence for selection was also re-evaluated using Haploplotter( url: <hg-wen.uchicago.edu/ selection/haplotter>) (Voight et al., 2006) which uses HapMap project data. The case-control study comparisons for associations were made on Stata v10 (StataCorp, College Station, TX) by unconditional logistic regression.

We tested HWE for genotypic counts of cases, under the assumption that the genotypic counts of controls are under HWE (Cui, 2000). When any locus was not in HWE, instead of dismissing the results, we used the genotype-based trend test (additive model) which does not rely on HWE (Sasieni, 1997) and reveals associations that depend additively upon the minor allele. This test compares the heterozygote and then homozygote frequencies with the wildtype homozygote frequency, and yields a "per allele odds ratio" (OR) for stepwise change per number of minor alleles in the genotype.

All patents, publications, accession numbers, and patent application described supra in the present application are hereby incorporated by reference in their entirety.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

References

1. Albig W, Drabent B, Burmester N, Bode C, Doenecke D. The haemochromatosis candidate gene HFE (HLA-H) of man and mouse is located in syntenic regions within the histone gene cluster. J Cell Biochem 1998; 69(2):117-26.
2. Assié G, LaFramboise T, Platzer P, Eng C. Frequency of germline genomic homozygosity associated with cancer cases. JAMA 2008; 299(12):1437-45.
3. Barrett J C, Fry B, Mailer J, Daly M J. Haploview: analysis and visualization of LD and haplotype maps. Bioinformatics 2005; 21(2):263-265.
4. Campbell H, Carothers A D, Rudan I, Hayward C, Biloglav Z, Barac L, Pericic M, Janicijevic B, Smolej-Narancic N, Polasek O, Kolcic I, Weber J L, Hastie N D, Rudan P, Wright A F. Effects of genome-wide heterozygosity on a range of biomedically relevant human quantitative traits. Hum Mol Genet 2007; 16(2):233-41.
5. Cardoso C S, Alves H, Mascarenhas M, Gonçalves R, Oliveira P, Rodrigues P, Cruz E, de Sousa M, Porto G. Co-selection of the H63D mutation and the HLA-A29 allele: a new paradigm of linkage disequilibrium? Immunogenetics 2002; 53(12):1002-8.
6. Cui J. Hardy-Weinberg equilibrium test in case-control studies. Stata Tech Bull 2000; 57:17-19.
7. Distante S, Robson K J, Graham-Campbell J, Arnaiz-Villena A, Brissot P, Worwood M. The origin and spread of the HFE-C282Y hemochromatosis mutation. Hum Genet 2004; 115:269-79.
8. Dorak M T. HFE H63D variant and leukemia susceptibility. Leuk Lymphoma 2006; 47(11):2269-70.
9. Dorak M T, Burnett A K, Worwood M, Sproul A M, Gibson B E. The C282Y mutation of HFE is another male-specific risk factor for childhood acute lymphoblastic leukemia. Blood 1999; 94(11):3957.
10. Dorak M T, Lawson T, Machulla H K, Mills K I, Burnett A K. Increased heterozygosity for MHC class H lineages in newborn males. Genes Immun 2002; 3(5):263-9.
11. Dorak M T, Burnett A K, Worwood M. HFE gene mutations in susceptibility to childhood leukemia: HuGE review. Genet Med 2005; 7(3):159-68.
12. Dorak M T, MacKay R, Relton C L, Worwood M, Parker L, Hall A G. Iron-related gene variants increase childhood leukemia risk and birth weight (abstract). Presented at the 57th Annual Meeting of the American Society for Human Genetics 2007 (San Diego, Calif.).
13. Edgren G, Nyrén 0, Melbye M. Cancer as a ferrotoxic disease: are we getting hard stainless evidence? J Natl Cancer Inst 2008; 100(14):976-7.
14. Fisher S A, Hampe J, Macpherson A J, Forbes A, Lennard-Jones J E, Schreiber S, Curran M E, Mathew C G, Lewis C M. Sex stratification of an inflammatory bowel disease genome search shows male-specific linkage to the HLA region of chromosome 6. Eur J Hum Genet 2002; 10(4):259-65.
15. Gubbels Bupp M R, Jørgensen T N, Kotzin B L. Identification of candidate genes that influence sex hormone-dependent disease phenotypes in mouse lupus. Genes Immun 2008; 9(1):47-56.
16. Hannuksela J, Savolainen E R, Koistinen P, Parkkila S. Prevalence of HFE genotypes, C282Y and H63D, in patients with hematologic disorders. Haematologica 2002; 87(2):131-5.
17. Horton R, Wilming L, Rand V, Lovering R C, Bruford E A, Khodiyar V K, Lush M J, Povey S, Talbot C C Jr, Wright M W, Wain H M, Trowsdale J, Ziegler A, Beck S. Gene map of the extended human MHC. Nat Rev Genet 2004; 5(12): 889-99.
18. Junne, K-T. Studies at the hemochromatosis (HFE) locus: gene conversions, haplotypes, and association analysis. Thesis (Ph. D.), Massachusetts Institute of Technology, Dept. of Biology, 2006 (URL: http://hdl.handle.net/1721.1/34193).
19. Kaminsky Z, Wang S C, Petronis A. Complex disease, gender and epigenetics. Ann Med 2006; 38(8):530-44.
20. Middleton D, Meenagh A, Gourraud P A. KIR haplotype content at the allele level in 77 Northern Irish families. Immunogenetics 2007; 59(2):145-58.
21. Porto G, Alves H, Rodrigues P, Cabeda J M, Portal C, Ruivo A, Justiça B, Wolff R, De Sousa M. Major histocompatibility complex class I associations in iron overload: evidence for a new link between the HFE H63D mutation, HLA-A29, and non-classical forms of hemochromatosis. Immunogenetics 1998; 47(5):404-10.
22. Rochette J, Pointon J J, Fisher C A, Perera G, Arambepola M, Arichchi D S, De Silva S, Vandwalle J L, Monti J P, Old J M, Merryweather-Clarke A T, Weatherall D J, Robson K J. Multicentric origin of hemochromatosis gene (HFE) mutations. Am J Hum Genet 1999; 64(4):1056-62.
23. Ruiz-Argüelles G J, Morales-Toquero A, Cruz-Dominguez G, Reyes-Núñez V, López-Martínez B, Ruiz-Delgado G J, Garcés-Eisele J. HFE-codon 63/282 (H63D/C282Y) gene variants in Mexican Mestizos are not risk factors for leukemia. Arch Med Res 2006; 37(1):65-7.
24. Sasieni P D. From genotypes to genes: doubling the sample size. Biometrics 1997; 53:1253-61.
25. Stevens R G, Graubard B I, Micozzi M S, Neriishi K, Blumberg B S. Moderate elevation of body iron level and increased risk of cancer occurrence and death. Int J Cancer 1994; 56(3):364-9.
26. Toomajian C, Ajioka R S, Jorde L B, Kushner J P, Kreitman M. A method for detecting recent selection in the human genome from allele age estimates. Genetics 2003; 165(1):287-97.
27. Yuan H Y, Chiou J J, Tseng W H, Liu C H, Liu C K, Lin Y J, Wang H H, Yao A, Chen Y T, Hsu C N. FASTSNP: an always up-to-date and extendable service for SNP function analysis and prioritization. Nucleic Acids Res 2006; 34:W635-41.
28. Williams S K, Tyler J K. Transcriptional regulation by chromatin disassembly and reassembly. Curr Opin Genet Dev 2007; 17(2):88-93.
29. Voight B F, Kudaravalli S, Wen X, Pritchard J K. A map of recent positive selection in the human genome. PLoS Biology 2006; 4(3): e72.
30. Worwood M, Raha Chowdhury R, Robson K J, Pointon J, Shearman J D, Darke C. The HLA A1-B8 haplotype extends 6 Mb beyond HLA-A: associations between HLA-A, B, F and 15 microsatellite markers. Tissue Antigens 1997; 50(5):521-6.

31. Xie T, Rowen L, Aguado B, Ahearn M E, Madan A, Qin S, Campbell R D, Hood L. Analysis of the gene-dense major histocompatibility complex class III region and its comparison to mouse. Genome Res 2003; 13(12):2621-26.

32. Zhou L, Myers A N, Vandersteen J G, Wang L, Wittwer C T. Closed-tube genotyping with unlabeled oligonucleotide probes and a saturating DNA dye. Clin Chem 2004; 50 (8):1328-35.

TABLE 1

HFE region haplotypes [1] determined in the population sample and homozygous cell line samples

| Haplotype | Frequency | (1) [2] rs8384 (HIST1H1C) | (2) rs10425 (HIST1H1C) | (3) rs9393682 | (4) rs9358903 | (5) rs807212 [3] | (6) rs2050947 | rs4529296 [4] (7) rs1800702 (8) rs2794720 rs2794719 [4] | (9) rs9366637 |
|---|---|---|---|---|---|---|---|---|---|
| 1 | 0.283 | 1 | 2 | 1 | 1 | 2 | 1 | 1 | 1 |
| 2 | 0.128 | 1 | 1 | 1 | 1 | 1 | 1 | 1 | 1 |
| 3 | 0.114 | 2 | 1 | 1 | 2 | 1 | 1 | 2 | 1 |
| 4 | 0.089 | 1 | 1 | 1 | 2 | 1 | 1 | 2 | 1 |
| 5 | 0.083 | 1 | 1 | 1 | 1 | 1 | 1 | 1 | 1 |
| 6 | 0.071 | 1 | 1 | 2 | 2 | 1 | 2 | 2 | 2 |
| 7 | 0.045 | 2 | 1 | 1 | 2 | 1 | 1 | 2 | 1 |
| 8 | 0.017 | 1 | 2 | 1 | 1 | 1 | 1 | 1 | 1 |
| 9 | 0.012 | 1 | 1 | 1 | 1 | 1 | 1 | 1 | 1 |
| 10 | 0.012 | 2 | 1 | 1 | 2 | 1 | 1 | 2 | 2 |
| 11 | 0.012 | 1 | 2 | 1 | 1 | 1 | 1 | 1 | 1 |

| Haplotype | (10) rs1799945 (H63D) | (11) rs2071303 | (12) rs1800562 (C282Y) | (13) rs2858996 | (14) rs707889 | (15) rs17596719 | (16) rs198853 (HIST1H4C) | (17) rs198844 (HIST1H1T) | Cell Lines |
|---|---|---|---|---|---|---|---|---|---|
| 1 | 1 | 1 | 1 | 1 | 1 | 1 | 2 | 2 | n = 11 [5] |
| 2 | 1 | 2 | 1 | 1 | 1 | 1 | 1 | 1 | n = 5 [6] |
| 3 | 1 | 1 | 1 | 2 | 2 | 1 | 1 | 2 | n = 6 [7] |
| 4 | 2 | 2 | 1 | 1 | 1 | 1 | 1 | 1 | n = 5 [8] |
| 5 | 1 | 1 | 1 | 1 | 1 | 2 | 1 | 1 | n = 7 [9] |
| 6 | 1 | 2 | 1 | 1 | 1 | 1 | 1 | 1 | n = 10 [10] |
| 7 | 1 | 1 | 2 | 2 | 2 | 1 | 1 | 2 | n = 2 [11] |
| 8 | 2 | 2 | 1 | 1 | 1 | 1 | 1 | 1 | PITOUT |
| 9 | 1 | 1 | 1 | 1 | 1 | 1 | 1 | 1 | ND [12] |
| 10 | 1 | 1 | 1 | 1 | 1 | 1 | 1 | 2 | ND |
| 11 | 1 | 2 | 1 | 1 | 1 | 1 | 1 | 1 | ND |

[1] '2' denotes minor allele, however, for the HIST1H1T SNP, allele G, which is in LD with C282Y and no longer the minor allele in Europeans is coded as 2. Minor alleles that occurred in only one of the haplotypes detected in the population sample at greater than 1% frequency are shown in bold (these alleles therefore tag their respective haplotypes).
[2] These SNP numbers correspond to the numbers used in Supplementary FIG. 1.
[3] The SNPs rs9467664, rs2213284, rs2230655 and rs12346 yielded identical results and not shown separately (see text).
[4] rs4529296 and rs2794719 were only genotyped in cell lines (rs1800560 encoding S65C was also genotyped in cell lines only but not shown in this table; see text).
[5] Haplotype 1: KAS011, QBL, BOLETH, BSM, MOU-MANN, KOSE, WT47, OLGA, AWELLS, MT14B, FUR.
[6] Haplotype 2: DUCAF, J0528239, HOR, PF04015, EAV.
[7] Haplotype 3: JESTHOM, WJR076, MGAR, BM21, BM9, MADURA.
[8] Haplotype 4: COX, SAVC, JVM, BRIP, CALOGERO.
[9] Haplotype 5: E4181324, RSH, SPO010, TISI, DBB, EK, MANIKA.
[10] Haplotype 6: VAVY, WT51, JHAF, BOB, LBF, LZL, KT14, WHONP439, WHONP192, AKIBA.
[11] Haplotype 7: WT100BIS, HO301.
[12] ND = not detected in any homozygous cell line.

TABLE 2

Features of studied SNPs located in the HFE region in chromosome 6 short arm

| SNP number | Location | Reference chromosome position [4] and nucleotide substitution | Relevance | Minor allele frequency (HapMap frequencies) [8] |
|---|---|---|---|---|
| rs9467664 [1] | 5' flanking region of HIST1H4A | 26 129 792 (T > A) | unknown | na [1] (0.356 - 0.089 - 0.089 - 0.033) |
| rs2213284 [1] | HIST1H3B (3' UTR) | 26 139 847 (T > C) | unknown | na [1] (0.356 - 0.100 - 0.091 - 0.033) |
| rs2230655 [1] | HIST11H2AB (L97L) | 26 141 485 (T > C) | synonymous coding region | na [1] (0.356 - 0.100 - 0.080 - 0.033) |
| rs8384 | HIST1H1C (P195P) | 26 164 051 (G > C) | synonymous coding region; ht SNP [5] | 0.208 (0.200 - 0.156 - 0.067 - 0.050) |
| rs10425 | HIST1H1C (S36S) | 26 164 528 (G > A) | synonymous coding region; ht SNP [5] | 0.335 (0.386 - 0.100 - 0.091 - 0.035) |
| rs9393682 | 3' flanking region of HIST1H1C | 26 165 029 (C > T) | unknown | 0.090 (0.049 - 0.526 - 0.590 - 0.042) |

TABLE 2-continued

Features of studied SNPs located in the HFE region in chromosome 6 short arm

| SNP number | Location | Reference chromosome position [4] and nucleotide substitution | Relevance | Minor allele frequency (HapMap frequencies) [8] |
|---|---|---|---|---|
| rs9358903 | 3' flanking region of HIST1H1C | 26 169 128 (A > C) | unknown; ht SNP [5] | 0.407 (0.431 - 0.807 - 0.789 - 0.167) |
| rs807212 | 3' flanking region of HIST1H1C | 26 173 600 (C > T) | unknown | 0.323 (0.358 - 0.089 - 0.091 - 0.042) |
| rs2050947 | 3' flanking region of HIST1H1C | 26 178 058 (G > C) | unknown | 0.084 (0.083 - 0.533 - 0.570 - 0.042) |
| rs4529296 [1] | 5' flanking region of HFE | 26 191 114 (C > G) | unknown | na [1] (0.400 - 0.733 - 0.663 - 0.155) |
| rs1800702 | 5' flanking region of HFE | 26 194 442 (C > G) | unknown | 0.393 (0.400 - 0.733 - 0.670 - 0.158) |
| rs2794720 | 5' flanking region of HFE | 26 195 181 (C > G) | unknown | 0.394 (0.397 - 0.733 - 0.670 - 0.147) |
| rs2794719 [1] | HFE intron 1 | 26 196 869 (T > G) | htSNP [5] | na [1] (0.405 - 0.733 - 0.670 - 0.147) |
| rs9366637 | HFE intron 1 | 26 197 077 (C > T) | intronic enhancer [6] | 0.087 (0.085 - 0.533 - 0.568 - 0.042) |
| rs1799945 | HFE exon 2 (H63D) | 26 199 158 (C > G) | missense substitution | 0.141 (0.129 - 0.023 - 0.022 - 0.0) |
| rs1800730 [1] | HFE exon 2 (S65C) | 26 199 164 (A > T) | missense substitution | na [1] (0.025 - 0.0 - 0.0 - 0.0) |
| rs2071303 [2] | HFE intron 2 | 26 199 315 (A > G) | ht SNP [5]; splice site variant [7] | 0.382 (0.367 - 0.700 - 0.789 - 0.308) |
| rs1800562 | HFE exon 4 (C282Y) | 26 201 120 (G > A) | missense substitution | 0.063 (0.042 - 0.0 - 0.0 - 0.0) |
| rs2858996 | HFE intron 5 | 26 202 005 (G > T) | intronic enhancer | 0.180 (0.195 - 0.136 - 0.067 - 0.078) |
| rs707889 | HFE intron 6/3' flanking [3] | 26 203 910 (G > A) | ht SNP [5] | 0.203 (0.200 - 0.144 - 0.068 - 0.292) |
| rs12346 [1] | 3' flanking region of HFE | 26 205 025 (G > A) | unknown | na [1] (0.362 - 0.800 - 0.818 - 0.931) |
| rs17596719 | 3' flanking region of HFE | 26 205 173 (G > A) | unknown | 0.096 (0.083 - 0.056 - 0.056 - 0.008) |
| rs198853 | 5' flanking region of HIST1H4C | 26 212 075 (T > C) | htSNP | 0.311 (0.350 - 0.100 - 0.089 - 0.100) |
| rs198844 | HIST1H1T (L14V) | 26 216 261 (G > C) | missense substitution and splice site variant [7] | 0.476 [9] (0.450 - 0.756 - 0.864 - 0.608) |

[1] The SNPs rs9467664, rs2213284, rs2230655, rs4529296, rs2794719, rs1800730 and rs12346 were genotyped in the cell line panel only.
[2] Formerly rs17515611.
[3] Located within intron 6 or 3' flanking region depending on the isoform.
[4] Chromosome 6 position is from NCBI ENTREZ SNP Reference Sequence (contig no: NT_007592.14).
[5] Haplotype tagging SNP in HapMap project data.
[6] FastSNP analysis suggested that this variant may alter Oct-1 transcription binding site.
[7] FastSNP analysis suggested that this variant may alter a splicing site.
[8] Minor allele frequency is from newborn controls in the present study and HapMap frequencies for comparison are for the populations: CEU-European; CHB-Han Chinese; JPT-Japanese; YRI-Yoruba.
[9] According to HapMap data, the minor allele of this SNP in Europeans is C and its frequency is given here (allele G is in LD with C282Y). In other populations, however, allele G is the minor allele.

TABLE 3

Hardy-Weinberg equilibrium and parameters of linkage disequilibrium with C282Y of the 17 SNPs genotyped in the control population sample

| SNP | HWE (P) | D'/LOD/r²/Δ [1] |
|---|---|---|
| rs8384 (1) [2] | 0.002 | 0.936/18.7/0.235/+0.022 |
| rs10425 (2) | 0.82 | 1.0/3.6/0.034/(−0.010) [3] |
| rs9393682 | 0.04 | 0.277/0.05/<0.01/−0.001 |
| rs9358903 (3) | 0.19 | 1.0/10.8/0.101/+0.020 |
| rs807212 (4) | 0.48 | 0.741/1.3/0.018/(−0.007) [3] |
| rs2050947 | 0.49 | 0.848/0.32/<0.01/+0.002 |
| rs1800702 (5) | 0.21 | 1.0/11.3/0.103/+0.019 |
| rs2794720 (6) | 0.38 | 1.0/9.8/0.102/+0.018 |
| rs9366637 (7) | 0.13 | 0.438/0.09/<0.01/(−0.001) [3] |
| rs1799945 (8) | 0.004 | 1.0/1.2/<0.01/(−0.004) [3] |
| rs2071303 (9) | 0.94 | 1.0/3.8/0.041/(−0.011) [3] |
| rs1800562 (10) | 0.44 | — |
| rs2858996 (11) | 0.0008 | 0.814/15.1/0.206/+0.021 |
| rs707889 (12) | 0.02 | 0.936/18.7/0.223/+0.022 |
| rs17596719 (13) | 0.02 | 1.0/1.5/<0.01/(−0.005) [3] |
| rs198853 | 0.92 | 1.0/2.81/0.029/0.016 |
| rs198844 (14) | 0.60 | 1.0/7.0/0.062/+0.016 |

[1] Burrows delta value for pairwise LD obtained on PopGene.
[2] Numbers in paranthesis refer to the position in haplotype frequency chart and LD plot (Supplementary FIG. 1).
[3] Statistically non-significant difference from Δ = 0.0 (P > 0.05).

TABLE 4

Ewens-Watterson neutrality test results on SNPs genotyped in 414 healthy newborn samples (obtained from 100 000 simulations)

| SNP | Observed F [1] | Minimum F-Maximum F | Mean (SE) | L95-U95 |
|---|---|---|---|---|
| rs8384 | 0.6709 | 0.5000-0.9973 | 0.8609 (0.0270) | 0.5043-0.9973 |
| rs10425 | 0.5543 | 0.5000-0.9972 | 0.8596 (0.0272) | 0.5039-0.9972 |
| rs9393682 | 0.8355 | 0.5000-0.9975 | 0.8621 (0.0270) | 0.5039-0.9975 |
| rs9358903 | 0.5173 | 0.5000-0.9971 | 0.8596 (0.0272) | 0.5037-0.9971 |
| rs807212 | 0.5626 | 0.5000-0.9975 | 0.8628 (0.0270) | 0.5041-0.9975 |
| rs2050947 | 0.8465 | 0.5000-0.9975 | 0.8618 (0.0271) | 0.5040-0.9975 |
| rs1800702 | 0.5231 | 0.5000-0.9972 | 0.8602 (0.0272) | 0.5039-0.9972 |
| rs2794720 | 0.5223 | 0.5000-0.9970 | 0.8585 (0.0273) | 0.5037-0.9970 |
| rs8366637 | 0.8407 | 0.5000-0.9974 | 0.8616 (0.0270) | 0.5042-0.9974 |
| rs1799945 | 0.7576 | 0.5000-0.9975 | 0.8628 (0.0270) | 0.5040-0.9975 |
| rs2071303 | 0.5281 | 0.5000-0.9971 | 0.8607 (0.0270) | 0.5043-0.9971 |
| rs1800562 | 0.8820 | 0.5000-0.9976 | 0.8616 (0.0272) | 0.5040-0.9976 |
| rs2858996 | 0.7046 | 0.5000-0.9972 | 0.8600 (0.0272) | 0.5040-0.9972 |
| rs707889 | 0.6760 | 0.5000-0.9974 | 0.8625 (0.0269) | 0.5045-0.9974 |
| rs17596719 | 0.8268 | 0.5000-0.9973 | 0.8616 (0.0269) | 0.5041-0.9973 |
| rs198853 | 0.5717 | 0.5000-0.9975 | 0.8622 (0.0269) | 0.5041-0.9975 |
| rs198844 | 0.5012 | 0.5000-0.9973 | 0.8618 (0.0270) | 0.5042-0.9973 |

[1] An observed F value outside the L95 and U95 range is an indication of natural selection ($P < 0.05$).

TABLE 5

IHWG HLA-typed Reference Cell Line Samples

| IHWG No | Cell Line Name | Population Origin |
|---|---|---|
| 9001 | SA | Japanese |
| 9004 | JESTHOM | Scandinavian |
| 9006 | WT100BIS | Italian |
| 9008 | DO208915 | Australian Caucasoid |
| 9009 | KAS011 | Yugoslavian |
| 9011 | E4181324 | Australian Caucasoid |
| 9012 | WJR076 | USA White |
| 9014 | MGAR | USA Hispanic |
| 9016 | RML REM | South American Indian |
| 9019 | DUCAF | French |
| 9020 | QBL | Dutch |
| 9021 | RSH, RSHD | African Black |
| 9022 | COX | South African White |
| 9023 | VAVY | French |
| 9026 | YAR | Ashkenazi Jewish |
| 9027 | PF97387 | French |
| 9028 | PE117 | Amerindian |
| 9029 | WT51 | Italian |
| 9030 | JHAF (JHF) | English |
| 9031 | BOLETH BO | Scandinavian |
| 9032 | BSM | Dutch |
| 9034 | SAVC | French |
| 9035 | JBUSH | USA White |
| 9036 | SPO010 | Italian |
| 9039 | JVM | Dutch |
| 9041 | J0528239 | Italian |
| 9042 | TISI | French |
| 9043 | BM21 | Italian |
| 9044 | BRIP | Italian |
| 9045 | TUBO | French |
| 9047 | PLH | Scandinavian |
| 9050 | MOU-MANN | Scandinavian |
| 9051 | PITOUT | South African White |
| 9052 | DBB | USA White |
| 9053 | HOR | Japanese |
| 9054 | EK EK(OH) | Scandinavian |
| 9055 | HO301 | French |
| 9056 | KOSE | German |
| 9059 | SLE005 | USA White |
| 9060 | CB6B-CGB1B | Australian Caucasoid |
| 9063 | WT47 | Italian |
| 9066 | TAB089, TAB | Japanese |
| 9068 | BM9 | Italian |
| 9069 | MADURA | Scandinavian |
| 9071 | OLGA | South American Indian |
| 9075 | DKB | Dutch |
| 9076 | T7526 | Chinese |
| 9079 | LWAGS | Ashkenazi Jewish |
| 9084 | CALOGERO | Italian |
| 9088 | PF04015 | French |
| 9089 | BOB | German |
| 9090 | AWELLS | Australian Caucasoid |
| 9092 | BM92 | Italian |
| 9093 | BER | German |
| 9094 | CF996 | French |
| 9096 | LBF-LBUF | English |
| 9097 | EMJ | USA White |
| 9098 | MT14B | Australian Caucasoid |
| 9099 | LZL | South American Indian |
| 9103 | KT14, LKT14 | Japanese |
| 9105 | FPAF FPF F | Ashkenazi Jewish |
| 9106 | MANIKA | Tamil Asian Indian |
| 9107 | KT3, LKT3 | Japanese |
| 9108 | CAR, ML | Unknown |
| 9109 | PIN, LJ | White |
| 9127 | MER, P | Unknown |
| 9136 | SPE, G | White |
| 9139 | WHONP439 | Asian |
| 9140 | WHO-NP192 | Asian |
| 9143 | KAWASAKI | Asian |
| 9145 | FUR, RE | White |
| 9146 | COL, E | Unknown |
| 9150 | BOW, MF | Unknown |
| 9151 | EAV, AC | Unknown |
| 9153 | WBD001088 | Unknown |
| 9157 | HAU, ML | Asian |
| 9179 | BSH012 | Unknown |
| 9286 | AKIBA | Japanese |
| 9290 | BON | French |
| 9301 | PRIESS | Danish |
| 9305 | WT46 | Italian |
| 9318 | PGF | English |

TABLE 6

List of 26 SNPs tightly in linkage disequilibrium
over 152 kb around the HFE gene (HapMap data)

| SNP | Gene | $r^2$ (with rs807212) | HWE (P) | Nucleotide position | Nucleotide Substitution | MAF (CEU-YRI) [1] |
|---|---|---|---|---|---|---|
| rs115810 | TRIM38-IVS7 | 0.929 | 0.16 | 26,083,862 | G > C | 0.342/0.033 |
| rs6901039 | intergenic | 0.929 | 0.16 | 26,108,864 | T > G | 0.342/0.350 |
| rs199753 | intergenic | 0.927 | 0.25 | 26,109,867 | T > C | 0.336/0.033 |
| rs199752 | intergenic | 0.962 | 0.08 | 26,120,854 | T > C | 0.336/0.033 |
| rs199751 | intergenic | 0.964 | 0.11 | 26,123,562 | T > C | 0.350/0.035 |
| rs199750 | HIST1H1A 3' | 0.964 | 0.50 | 26,124,441 | T > C | 0.350/0.033 |
| rs9467664 | HIST1H4A 5' | 1 | 0.10 | 26,129,792 | T > A | 0.356/0.033 |
| rs9358901 | intergenic | 0.965 | 0.17 | 26,132,415 | T > G | 0.367/0.382 |
| rs1540276 | intergenic | 1 | 0.08 | 26,136,798 | C > A | 0.358/0.037 |
| rs2213284 | HIST1H3B 3'UTR | 1 | 0.08 | 26,139,847 | T > C | 0.358/0.033 |
| rs2230655 | HIST1 H2AB L97L | 1 | 0.08 | 26,141,485 | T > C | 0.358/0.033 |
| rs4401650 | intergenic | 0.963 | 0.25 | 26,143,187 | G > A | 0.362/0.043 |
| rs1540275 | intergenic | 1 | 0.08 | 26,144,455 | G > A | 0.362/0.043 |
| rs2032447 | HIST1H3C 5' | 0.861 | 0.89 | 26,152,348 | C > T | 0.395/0.433 |
| rs7756117 | HIST1H3C 3' | 0.963 | 0.25 | 26,154,544 | A > G | 0.362/0.310 |
| rs10425 | HIST1H1C S36S | 0.894 | 0.29 | 26,164,528 | C > T | 0.386/0.035 |
| rs807214 | HFE 5' | 0.931 | 0.12 | 26,169,748 | G > C | 0.375/0.033 |
| rs807212 | HFE 5' | (1) | 0.08 | 26,173,600 | C > T | 0.358/0.042 |
| rs12346 | HFE 3' | 0.963 | 0.12 | 26,205,025 | G > A | 0.353/0.034 |
| rs198853 | HIST1H4C 5' | 0.964 | 0.11 | 26,212,075 | T > C | 0.350/0.100 |
| rs198852 | HIST1H4C L91L | 0.821 | 0.16 | 26,212,427 | A > G | 0.377/0.108 |
| rs198848 | HIST1H1T 3' | 0.801 | 0.16 | 26,214,304 | G > A | 0.392/0.100 |
| rs198845 | HIST1H1T Q178K | 0.8 | 0.13 | 26,215,769 | G > T | 0.398/0.093 |
| rs198834 | intergenic | 0.801 | 0.16 | 26,222,351 | G > A | 0.392/0.033 |
| rs198820 | HIST1H2AC 5' | 0.826 | 0.24 | 26,232,222 | C > T | 0.388/0.059 |
| rs198815 | intergenic | 0.804 | 0.31 | 26,235,250 | A > G | 0.375/0.103 |

[1] CEU = European, YRI = African.

TABLE 7

HaploPlotter results showing the P values for the test of neutrality obtained from
HapMap data in three populations (CEU = European, YRI = African, ASN = Asian)

| Gene ID | Gene Name | Region | P (CEU) | P (YRI) | P (ASN) |
|---|---|---|---|---|---|
| 10590 | SCGN | 25760439-25809990 | 0.190026 | 0.607928 | 0.060467 |
| 221613 | HIST1H2AA | 25834270-25834734 | 0.541838 | 0.999955 | 0.043647 |
| 255626 | HIST1H2BA | 25835116-25835552 | 0.541838 | 0.999955 | 0.043647 |
| 10050 | SLC17A4 | 25862935-25888419 | 0.351631 | 0.999955 | 0.050227 |
| 6568 | SLC17A1 | 25891296-25938776 | 0.252749 | 0.408690 | 0.195580 |
| 10786 | SLC17A3 | 25953307-25990493 | 0.074535 | 0.408690 | 0.117922 |
| 10246 | SLC17A2 | 26020961-26038818 | 0.049735 | 0.170705 | 0.074738 |
| 10475 | TRIM38 | 26071050-26093337 | 0.026700 | 0.103382 | 0.043647 |
| 10338 | HIST1H1PS2 | 26124314-26125048 | 0.035480 | 0.079686 | 0.036697 |
| 3024 | HIST1H1A | 26125239-26125995 | 0.035480 | 0.079686 | 0.036697 |
| 8350 | HIST1H3A | 26128697-26129165 | 0.035480 | 0.079686 | 0.043647 |
| 8359 | HIST1H4A | 26129886-26130257 | 0.035480 | 0.063964 | — |
| 8366 | HIST1H4B | 26135103-26135459 | 0.030683 | — | 0.036697 |
| 8358 | HIST1H3B | 26139796-26140267 | 0.030683 | 0.063964 | 0.036697 |
| 8335 | HIST1H2AB | 26141299-26141775 | 0.026700 | — | 0.036697 |
| 3018 | HIST1H2BB | 26151434-26151864 | 0.030683 | 0.063964 | 0.043647 |
| 10341 | HIST1H2APS5 | 26152107-26152757 | 0.026700 | 0.063964 | 0.043647 |
| 8352 | HIST1H3C | 26153618-26154076 | 0.030683 | 0.063964 | 0.043647 |
| 3006 | HIST1H1C | 26163894-26164678 | 0.026700 | — | 0.036697 |
| 3077 | HFE | 26195427-26205038 | 0.041544 | 0.079686 | 0.036697 |
| 8364 | HIST1H4C | 26212140-26212544 | 0.061728 | 0.132766 | 0.043647 |
| 3010 | HIST1H1T | 26215619-26216343 | 0.074535 | 0.170705 | 0.036697 |
| 8334 | HIST1H2AC | 26232352-26232897 | 0.148074 | 0.225666 | 0.023723 |
| 3017 | HIST1H2BD | 26266328-26279556 | 0.148074 | 0.408690 | 0.014086 |

TABLE 8

Allele frequencies and association test results in the
117 childhood ALL cases and 414 newborn controls

| SNP number | Allele Frequencies (Cases vs Controls, P) ($P_{HWE}$ for adjusted HWE) | Additive Model (per allele OR (95% CI), P) |
|---|---|---|
| rs8384 | 0.234[1]-0.208[1]; P = 0.32<br>$P_{HWE}$ = 0.02 | 1.33 (0.81 to 1.58), P = 0.46 |
| rs10425 | 0.295-0.335; P = 0.27<br>$P_{HWE}$ = 0.31 | 0.84 (0.60 to 1.69), P = 0.29 |
| rs9393682 | 0.061-0.091; P = 0.21<br>$P_{HWE}$ = 0.24 | 0.68 (0.38 to 1.22), P = 0.20 |
| rs9358903 | 0.461-0.407; P = 0.13<br>$P_{HWE}$ = 0.05 | 1.22 (0.91 to 1.65), P = 0.19 |
| rs807212 | 0.227-0.328; P = 0.006<br>(in males: 0.154-0.305; P = 0.002)<br>$P_{HWE}$ = 0.0005 | 0.55 (0.38 to 0.79), P = 0.001 |
| rs2050947 | 0.061-0.084; P = 0.32<br>$P_{HWE}$ = 0.35 | 0.72 (0.40 to 1.31), P = 0.29 |
| rs1800702 | 0.385-0.393; P = 0.84<br>$P_{HWE}$ = 0.97 | 0.97 (0.70 to 1.34), P = 0.85 |
| rs2794720 | 0.455-0.394; P = 0.11<br>$P_{HWE}$ = 0.09 | 1.20 (0.74 to 1.97), P = 0.46 |
| rs9366637 | 0.071-0.087; P = 0.40<br>$P_{HWE}$ = 0.17 | 0.82 (0.47 to 1.43), P = 0.49 |
| rs1799945 | 0.190-0.122 [2,3]; P = 0.02<br>$P_{HWE}$ = 0.30 | 1.44 (0.92 to 2.25) P = 0.11 |
| rs2071303 | 0.385-0.382; P = 0.84<br>$P_{HWE}$ = 0.65 | 1.01 (0.74 to 1.40), P = 0.93 |
| rs1800562 | 0.090-0.063; P = 0.12<br>$P_{HWE}$ = 0.38 | 1.48 (0.87 to 2.52) P = 0.15<br>(in males: 2.03 (1.05 to 3.94), P = 0.04) |
| rs2858996 | 0.199-0.180 [1]; P = 0.50<br>$P_{HWE}$ = 0.02 | 1.11 (0.78 to 1.57), P = 0.57 |
| rs707889 | 0.224-0.203 [1]; P = 0.54<br>$P_{HWE}$ = 0.27 | 1.11 (0.79 to 1.57), P = 0.54 |
| rs17596719 | 0.130-0.096 [1]; P = 0.23<br>$P_{HWE}$ = 0.19 | 1.34 (0.87 to 2.05), P = 0.19<br>(in males: 2.0 (1.15 to 3.50), P = 0.02;<br>P for interaction with sex = 0.03) |
| rs198853 | 0.248-0.311; P = 0.09<br>$P_{HWE}$ = 0.19 | 0.73 (0.51 to 1.03), P = 0.08<br>(in males 0.60 (0.37 to 0.96), P = 0.03) |
| rs198844 | 0.486-0.524; P = 0.42<br>$P_{HWE}$ = 0.24 | 0.86 (0.64 to 1.17), P = 0.34 |

[1] Mild Hardy-Weinberg disequilibrium (0.05 < P < 0.001).
[2] Severe Hardy-Weinberg disequilibrium (P < 0.001).
[3] Due to total absence of H63D homozygotes in controls and presence of four homozygote cases.

What is claimed is:

1. A method for determining whether a human male child has a reduced risk of childhood acute lymphoblastic leukemia (ALL), comprising the steps of:
   (a) obtaining a biological sample from a human male child;
   (b) isolating nucleic acid from said biological sample;
   (c) performing a polymerase chain reaction-restriction fragment length polymorphism assay (PCR-RFLP) in the isolated nucleic acid obtained in (b), said PCR-RFLP comprises the steps of:
      (i) performing a PCR on said isolated nucleic acid to produce an amplicon containing haplotype tagging SNP rs807212; and
      (ii) digesting said amplicon with a restriction endonuclease to produce a plurality of fragments, wherein said restriction endonuclease is MspI;
   (d) determining heterozygosity for thymine (T) allele at said haplotype tagging SNP rs807212 in said amplicon based on the presence of said plurality of fragments; and
   (e) determining that said human male child has a reduced risk of childhood ALL based on said determined heterozygosity.

2. The method of claim 1, wherein said biological sample is cord blood or peripheral blood.

3. The method of claim 1, wherein said isolating step is performed using phenol-chloroform.

4. The method of claim 1, wherein said nucleic acid is genomic DNA.

* * * * *

SEQUENCE LISTING

<160> NUMBER OF SEQ ID NOS: 5

<210> SEQ ID NO 1
<211> LENGTH: 27
<212> TYPE: DNA
<213> ORGANISM: artificial sequence
<220> FEATURE:
<223> OTHER INFORMATION: primer

<400> SEQUENCE: 1
tctcaacctt agaccaactt atgtctt                                27

<210> SEQ ID NO 2
<211> LENGTH: 24
<212> TYPE: DNA
<213> ORGANISM: artificial sequence
<220> FEATURE:
<223> OTHER INFORMATION: primer

<400> SEQUENCE: 2
cattctccag ataatcccaa tact                                   24

```
-continued

<210> SEQ ID NO 3
<211> LENGTH: 22
<212> TYPE: DNA
<213> ORGANISM: artificial sequence
<220> FEATURE:
<223> OTHER INFORMATION: probe

<400> SEQUENCE: 3
tactgaaaca cgttccacag cc                                              22

<210> SEQ ID NO 4
<211> LENGTH: 20
<212> TYPE: DNA
<213> ORGANISM: artificial sequence
<220> FEATURE:
<223> OTHER INFORMATION: primer

<400> SEQUENCE: 4
cgagaagcga tggtcatttt                                                 20

<210> SEQ ID NO 5
<211> LENGTH: 20
<212> TYPE: DNA
<213> ORGANISM: artificial sequence
<220> FEATURE:
<223> OTHER INFORMATION: primer

<400> SEQUENCE: 5
ccttcatggt ggtgtttgaa                                                 20
```